(12) United States Patent
Denny et al.

(10) Patent No.: US 10,197,529 B2
(45) Date of Patent: Feb. 5, 2019

(54) METHODS AND SYSTEMS FOR VARIANT DETECTION

(71) Applicant: LIFE TECHNOLOGIES CORPORATION, Carlsbad, CA (US)

(72) Inventors: David A. Denny, Olney, MD (US); David Woo, Foster City, CA (US); Manjula Aliminati, Santa Clara, CA (US); Siva Kumar Samsani, Dublin, CA (US); Stephanie J. Schneider, Mountain View, CA (US); Yoke Peng Lim, Palo Alto, CA (US); Sylvia Chang, Fremont, CA (US)

(73) Assignee: Life Technologies Corporation, Carlsbad, CA (US)

( * ) Notice: Subject to any disclaimer, the term of this patent is extended or adjusted under 35 U.S.C. 154(b) by 278 days.

(21) Appl. No.: 15/130,532

(22) Filed: Apr. 15, 2016

(65) Prior Publication Data
US 2016/0313280 A1  Oct. 27, 2016

Related U.S. Application Data

(60) Provisional application No. 62/148,049, filed on Apr. 15, 2015.

(51) Int. Cl.
*G01N 27/447* (2006.01)
*G06F 19/22* (2011.01)

(52) U.S. Cl.
CPC ....... *G01N 27/44717* (2013.01); *G06F 19/22* (2013.01)

(58) Field of Classification Search
CPC .......................... G01N 27/44717; G06F 19/22
USPC ........................................................ 702/189
See application file for complete search history.

(56) References Cited

U.S. PATENT DOCUMENTS

| | | | |
|---|---|---|---|
| 2005/0059046 A1* | 3/2005 | LaBrenz | G06F 19/22 435/6.11 |
| 2006/0035253 A1* | 2/2006 | Sayer | C12Q 1/6869 435/6.14 |
| 2015/0032385 A1 | 1/2015 | Young et al. | |
| 2017/0235874 A1* | 8/2017 | Leong | G06F 19/18 702/20 |

FOREIGN PATENT DOCUMENTS

EP          1128311 A2     8/2001

* cited by examiner

*Primary Examiner* — Anthony Ho
(74) *Attorney, Agent, or Firm* — Mauriel Kapouytian Woods LLP; Elaine K. Lee; Michael Mauriel

(57) ABSTRACT

In one exemplary embodiment, a method for detecting variants in electropherogram data is provided. The method includes receiving electropherogram data from an instrument and analyzing the electropherogram data to identify mixed bases in the electropherogram data. The method further includes identifying features within the electropherogram data indicative of errors and validating the identified mixed bases. Then the method includes determining variants in the electropherogram data based on the validated mixed bases.

16 Claims, 47 Drawing Sheets

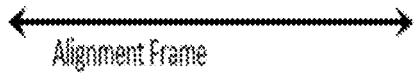

Alignment Frame

The alignment frame describes the pairing of the sample sequence, in the forward reading frame, with the reference sequence by defining the start and end of the aligned region on the query and on the reference sequence. Because there may be insertions and deletions, there is not a 1:1 mapping between each position on the query to the reference.

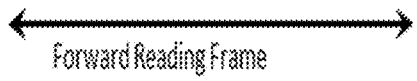

Forward Reading Frame

The Forward Reading is based on the Clear Reading frame and is oriented in a 5'-3' order of the sample. The sequence for forward reads is identical to those in the Base Call frame. The sequence for reverse reads a reversed and transposed.

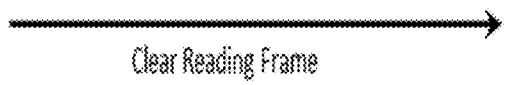

Clear Reading Frame

The Clear Reading frame describes the region of the KB called base frame which are of high-quality and should be considered for analysis. In some cases, the clear range is equivalent to the KB called base frame and does not imply any biological orientation or relationship with the reference frame.

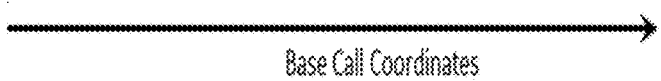

Base Call Coordinates

The Base Call coordinates provides the sequence of bases called by KB Caller corresponding the sequence of peaks in the Trace Coordinate frame. It begins with zero and ends with the index of the last base called. The numbers always ascend.

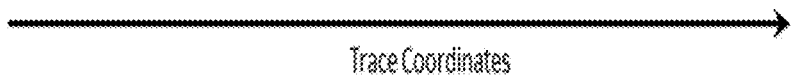

Trace Coordinates

The Trace Coordinate reference frame is defined as one electropherogram unit (EPU) for each sampled height of the signal. It begins with zero and ends at the conclusion of the sampling. The numbers always ascend by one from left to right. The order has no implication on the biological sense of the sample or relationship with the reference frame.

Reference Sequence Frame

The Reference Sequence frame indicates the sequence of bases. It may/may not begin with zero. The bases are always pure. The index always ascends by one from left to right.

FIG. 5

Pure-Base Assertion
Good pure base:
- Low overlap (<25%).
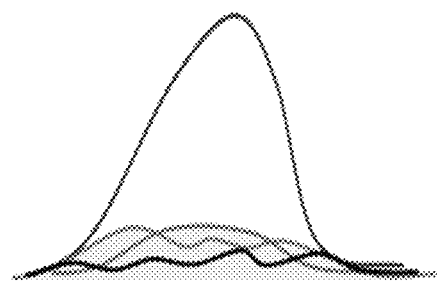
Poor pure base:
- High overlap (>25%) from another single trace
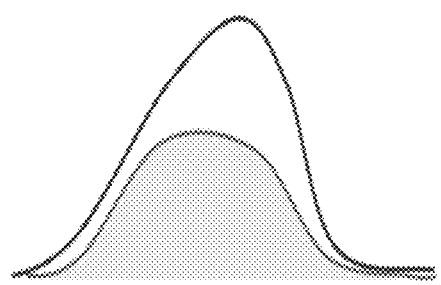
Poor pure base:
- High aggregate overlap (>25%) (note: calculation of total overlap limits height to highest point – not the sum of the overlaps.)
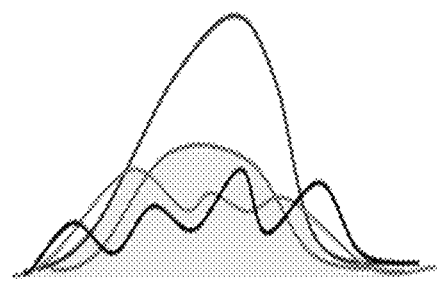
FIG. 26

Mixed-Base Assertion
Good mixed base:
- High overlap (>25%) of secondary peak.
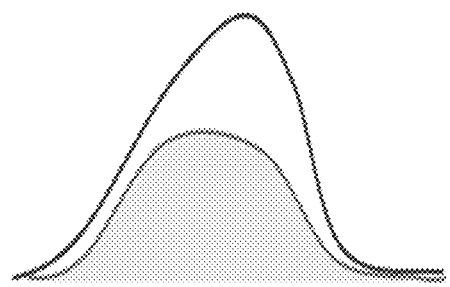
Poor mixed base:
- Low overlap (<25%) of secondary peak.
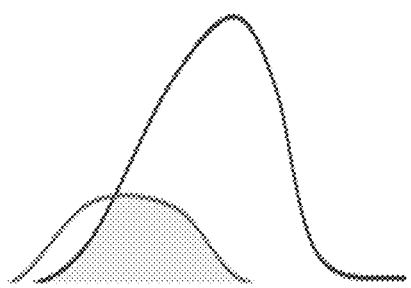
Poor mixed base:
- Overlap of secondary base is not distinguished from overlap of other traces
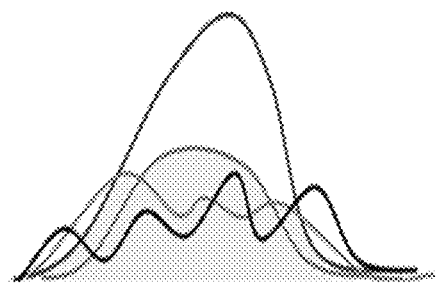
FIG. 28

METHODS AND SYSTEMS FOR VARIANT DETECTION

CROSS-REFERENCE TO RELATED APPLICATIONS

This application claims the benefit of priority of U.S. Provisional Patent Application No. 62/148,049 filed on Apr. 15, 2015, which is incorporated herein in its entirety by reference.

BACKGROUND

Technology invented by Fred Sanger has provided the mainstay of sequencing approaches since its inception in 1977, culminating with the release of the Human Genome sequence in 2000 by Human Genome Sciences. Sanger sequencing remains a valuable and viable research tool, but the challenge of interpreting instrument signals to produce high quality biological indication remain.

Basic operation of the Sanger sequencing equipment produces an electropherogram, a line plot with four traces that traverse horizontally and whose vertical axis records the amplitudes that reflect the level of detection of the four measured genomic bases: G, A, T, C. Progress along the horizontal position records regular digitized samples as the sample medium flows through the detection column, carrying with it the genomic (DNA) content. With high-quality traces, the central region of the electropherogram shows sequence of well-formed (Gaussian) peaks which are evenly spaced and have consistent amplitude, well-modulated above a low murmur of background noise. In some cases, two peaks will rise simultaneously and typically to a lower height than normal. This reports a mixed-base observation.

The ends of these traces record the initial introduction of the sample and the conclusion of the sample and are virtually always of lower quality, having irregular cadence and irregular and frequently lowered amplitude, and higher noise background. In many cases the peaks are no longer Gaussian in shape and may have overlapping regions. Quality trimming is generally applied to the traces to remove these low-quality regions, however it is often a compromise between preserving sequence and rejecting noise.

Low quality traces can occur due to sample contamination, low-quality primers, and many other experimental conditions. These can result in irregularities in otherwise high quality traces. Ink blobs are a characteristic of an irregularity and result in hugely exaggerated peaks which may span multiple underlying high-quality peaks.

Many researchers continue to trust expert human inspection of Sanger electropherograms for interpretation rather than trust to automated processing. The many characteristics of the electropherograms are hard to characterize algorithmically without a large body of highly qualified data to tune and develop the algorithms.

Humans are diploid organisms, meaning that we have two copies of each gene in our chromosome. In many cases these copies are heterozygous, or giving two different alleles of the same genes. With Sanger sequencing the sequence reflects this heterozygous condition with a combination of base values at the differentiating positions that is one allele may have an "A" base while one allele may have a "C" base, and this is represented as the mixed-base "M".

A goal of genomics analysis is to recover the true sequence of both alleles in the heterozygous case from Sanger sequencing, however the information available at secondary analysis is inadequate for accurate assignment of multiple heterozygous observations to alleles. Additionally, many mixed-base observations are the result of instrument noise and not true biological variation. The predominance of algorithms do not provide mechanism to accurately align mixed-base sequences to a reference sequence.

SUMMARY

In one exemplary embodiment, a method for detecting variants in electropherogram data is provided. The method includes receiving electropherogram data from an instrument and analyzing the electropherogram data to identify mixed bases in the electropherogram data. The method further includes identifying features within the electropherogram data indicative of errors and validating the identified mixed bases. Then the method includes determining variants in the electropherogram data based on the validated mixed bases.

DESCRIPTION OF THE FIGURES

FIG. 5 illustrates various reference frames according to various embodiments described herein;

FIG. 26 illustrates a pure base square score assertion according to various embodiments described herein;

FIG. 28 illustrates a mixed based square score assertion according to various embodiments described herein;

DETAILED DESCRIPTION

To provide a more thorough understanding of the present invention, the following description sets forth numerous specific details, such as specific configurations, parameters, examples, and the like. It should be recognized, however, that such description is not intended as a limitation on the scope of the present invention, but is intended to provide a better description of the exemplary embodiments.

According to various embodiments of methods and systems described herein, a number of innovative features to enable processing of mixed-base sequence data produced from Sanger instrumentation, to produce high-quality variant observations for subsequent investigation by researchers is provided.

Figure 1:
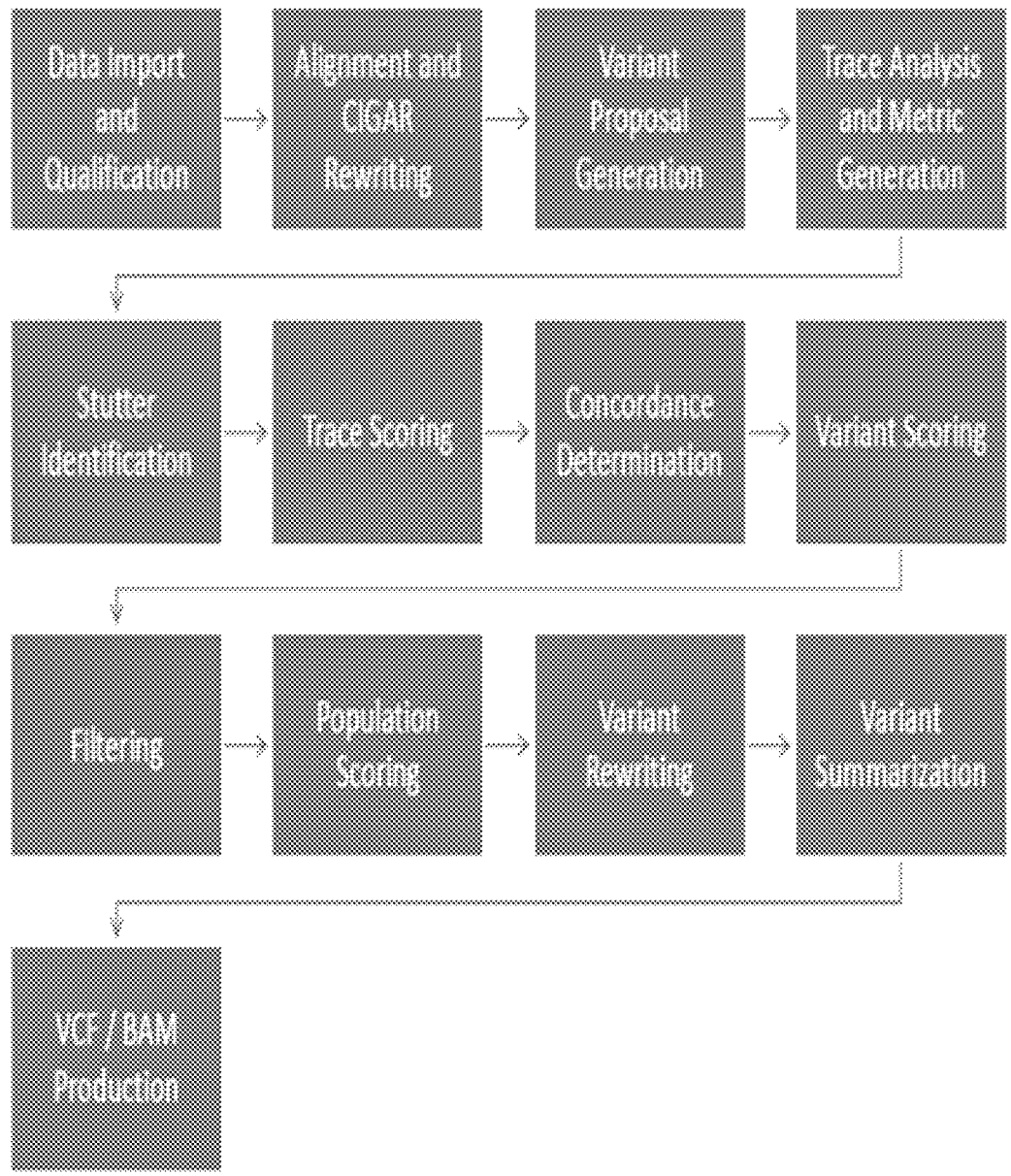
FIG. 1 illustrates a method of analyzing mixed bases according to various embodiments described herein.

FIG. 1 illustrates an exemplary workflow according to various embodiments described by the present teachings. In the method of FIG. 1, more accurate variant calling in electropherograms is achieved by analyzing and adjusting alignment, determining characteristics of the electropherogram trace that could lead to error, and various scoring determinations. These functions are described in more detail below.

A Mechanism for Mixed-Base Sequence Analysis Support

Figure 2:
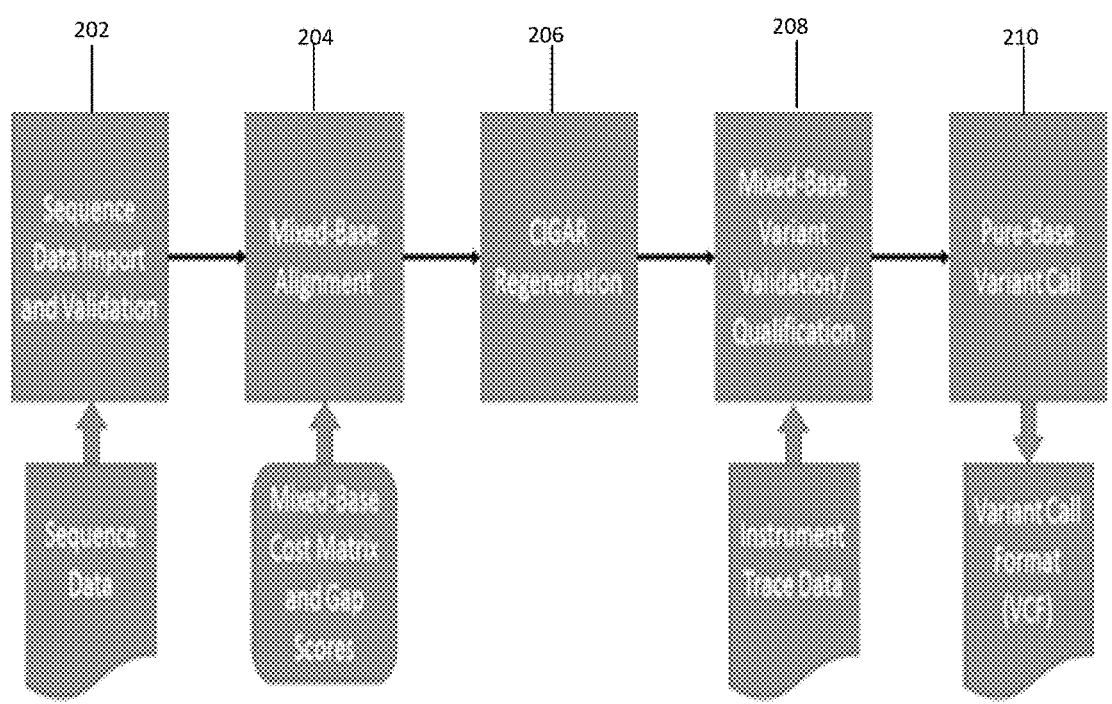
FIG. 2 illustrates a method of detecting variants according to various embodiments described herein.

Various embodiments of the present teachings described herein include the following features, also illustrated in FIG. 2:

1.) Importation of sequence data in step 202.
2.) Implementation of mixed-base support in high-performance, off-the-shelf Stripped Smith-Waterman algorithm to produce highly-accurate CIGAR string alignment representations in step 204.
3.) Regeneration of CIGAR to capture mixed-base (heterozygous) events in step 206.
4.) Validation and qualification of mixed-base observations using trace based analysis in step 208.
5.) Generation of pure-base variant calls for incorporation in standardized (VCF) output in step 210.

Implementation Mixed-Base Alignment Support

Query Sequence Import

According to various embodiments, in step 202, individual Sanger sequences (reads) are imported into Query Sequence Records from FASTA format and base call symbols are validated as indicating valid pure bases or valid mixed-bases on the terms of membership in a Base Translation Table. The Base Translation Table is derived from the public-source table contained in a library, Stripped Smith-Waterman alignment algorithm described in PLOS (Zhao M, 2013). However, according to various embodiments, the table has been resized and populated to incorporate mixed-base calls as well as pure base calls. If invalid base symbols are detected, the sequence is rejected and a warning is provided to the user. The FASTA header for the sequences is modified to support additional identifiers needed by the algorithms according to various embodiments described herein. Additionally, the header includes the untrimmed sequence length and the clear range definition. The processor employing the algorithm according to various embodiments will compare the length of the imported sequence to the length indicated by the modified FASTA formatted header. If a discrepancy exists, the read will be rejected and a warning issued.

Sequence Orientation Detection

The method according to various embodiments implements an Orientation Detection function which identifies imported sequences as being forward or reverse reading based on a preliminary alignment to the reference sequence. The Orientation Detection function is implemented using the National Center for Biotechnology Information (NCBI) Basic Local Alignment Search Tool (BLAST) algorithm, Megablast configuration. The BLAST algorithm is retrieved from the NCBI C++ Toolkit which is available from http://www.ncbi.nlm.nih.gov/toolkit/doc/book/ch_getcode_syn#ch_getcode_snv.ftp_download. According to various embodiments, the required modules from the NCBI C++ Toolkit in the Orientation Detection function provide high-speed and highly validated operation. The Orientation Detection Function determines the sequence orientation based on the BLAST scores and the orientation detected by the BLAST algorithm. Should the score fail to meet a criterion, the orientation of the sequence cannot be determined and the Orientation Detection function will reject sample and not produce an orientation record. The Orientation Detection function records the orientation findings in a tab-delimited transfer file which is used subsequence by the method of detecting variants. The file during the alignment processing is imported and validity of the file is determined. If a corruption in the format is detected, the alignment process is aborted. Additionally, an imported sequence record for each orientation record is checked.

An error will be provided if there is excessive orientation records or excessive sequence records.

Sequence Reorientation

During sequence import, sequences identified as into the forward reading frame are converted. This is done by reversing the order of the bases in the sequence and then obtaining the complement of the reversed bases by using two mapping arrays and a high-speed linear search algorithm to identify and translate the incoming base to its complement form, including mixed-base conversion.

Additional Sequence Validation

The sequences are further validated during import. The imported sequence length is qualified and sequences whose length falls below a certain threshold are rejected.

The ratio of the trimmed length is computed versus the untrimmed length of read and if the ratio falls below a threshold. Again, a warning will be issued to indicate that the sample quality is suspect.

Additionally, the number of mixed-bases contained in the sequence is counted. The ratio of mixed-bases to total sequence length is computed.

Should the ratio be excessive, a flag is set to imply further processing of the sequence. Any rejected sequences are maintained in a separate list of failed samples for later reporting.

Reference Sequence Import

The reference sequence is imported into a Reference Sequence Record from a FASTA formatted input. The reference is assumed in the forward reading frame. The reference is validated to contain only pure bases. The length of the reference sequence is validated against the length indicated in the modified FASTA header. Errors halt processing with a warning to the user.

Alignment Database

An Alignment Database is created to save the sequence Alignment Records according to various embodiments described herein. These Alignment Records contain reference to the Query Sequence Record and the Reference Sequence Reference as well as specific outcomes of the alignment operation. The database additionally is segregated to contain passing and failed Alignment Records.

Aligner Module

A module called Aligner is included in the method according to various embodiments. The Aligner integrates the functionality of the Stripped Smith-Waterman (SSW) alignment algorithm identified with functions and data storage schemes useful to facilitate mixed-base alignment for embodiments described herein.

Mixed-Base Alignment Configuration

Figure 3:
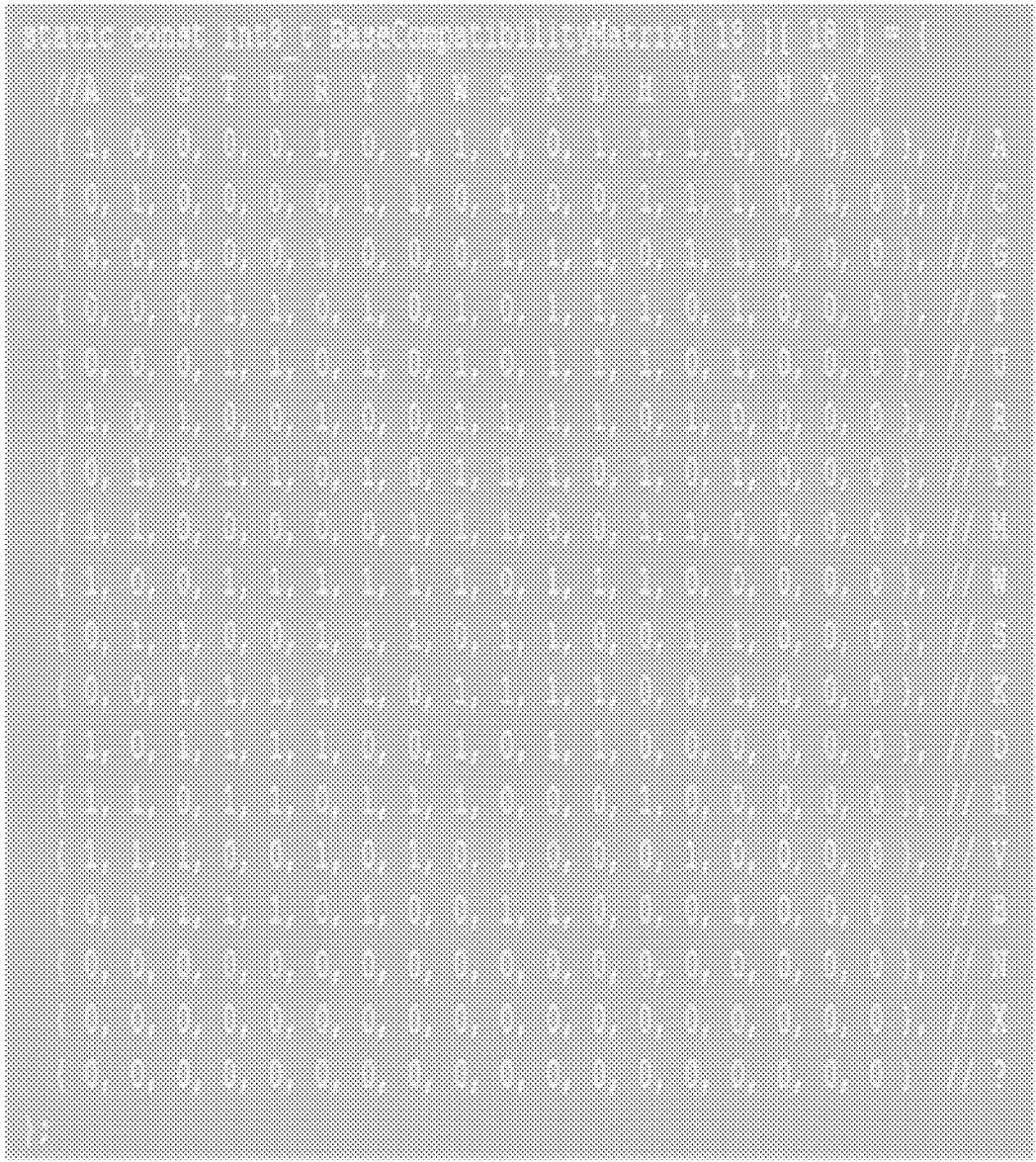
FIG. 3 illustrates a base compatibility matrix according to various embodiments described herein.

The SSW alignment algorithm is parameter driven and comes with default settings for pure-base alignment. Aligner defines additional configurations of predefined constants used by the SSW algorithm to facilitate mixed-based alignment in step 204, algorithm testing, and algorithm validation. The default operational configuration supports mixed-base alignment. In this mode the Aligner configures the SSW algorithm to accommodate mixed-base symbols through configuring a modified Base Translation Table (described above), a mixed-base cost matrix (below) and gap opening, gap extension, mismatch penalties and match reward which our testing has revealed to produce contigs (consecutive stretches of alignments) which favor generation of mismatches over gaps. Specifically, the SSW alignment algorithm will reward, rather than punish transitions between compatible bases. In order to determine compatibility of bases, the Aligner implements a compatible bases function. This function is optimized by first translating the two involved base symbols from the evaluated sequences (reference and query) into a base index using the Base Translation Table. Then using the indexes to determine the compatibility using the Base Compatibility Matrix, illustrated in FIG. 3.

For example, if an "A" is encountered in the reference and an "M" in the query, which are compatible, the SSW alignment algorithm will mark these bases as matching and will not open an alignment gap or impose a mismatch penalty. Aligner execution uses the SSW algorithm to identify the best fit between the reference and the query sequences and produces a Compact Idiosyncratic Gapped Alignment Report (CIGAR) string that describes the differences between the reference sequence and the query sequence in an alphanumeric format. To facilitate high-speed processing, the Aligner converts the CIGAR string produced by the SSW algorithm into a vector of CIGAR Operations, each of which is described as having a length and a type of: Match, Mismatch, Insert, and Deletion. The Aligner the stores the CIGAR along with the beginning and ending positions of the aligned portion of the query sequence and reference sequence into an Alignment Record which it then records into the Alignment Database.

CIGAR Regeneration Module

Because the mixed-base alignment operation has treated compatible mixed-bases as matches, and stored these in Match CIGAR Operations, the CIGAR Regeneration module is implemented in step 206 to identify compatible mixed-bases in a regenerated CIGAR as Mismatches CIGAR Operations. For each Alignment Record stored in the Alignment Database the CIGAR Regeneration module retrieves the CIGAR (Source CIGAR) and the Query Sequence Record. The CIGAR Regeneration module additionally creates a blank CIGAR (Target CIGAR) to hold the results of rewriting and also retrieve the relevant Query Sequence Record. For each Insert, Deletion, or Mismatch operation recorded in the Source CIGAR, the CIGAR Regeneration module creates an identical operation and inserts it into the Target CIGAR. For each Match operation in the Source CIGAR, the CIGAR Regeneration module examines the bases in the corresponding region of the Query Sequence Record to identify pure-bases and mixed-bases (described previously). The CIGAR Regeneration module aggregates the pure bases into a Match operation. If a mixed-base is encountered, the CIGAR Regeneration module terminates and emits any current Match operation, initiates a Mismatch operation, and aggregates all consecutive mixed-bases into the Mismatch operation. If a pure base should subsequently be encountered or if the end of the Match operation in the Source CIGAR is encountered, the CIGAR Regeneration module will emit the mismatch operation. When all the CIGAR Operations contained in the Source CIGAR have been processed and the matching (compatible) mixed-bases have been processed into Mismatch operations in the Target CIGAR, the CIGAR Regeneration module replaces the Source CIGAR with the Target CIGAR in the Alignment Database and proceeds to the next Alignment Record until all Alignment Records have been processed.

Alignment Score Calculation

The CIGAR Regeneration module provides an efficient opportunity to measure the quality of the resulting alignment of the query sequence and the reference sequence. During generation of the Target CIGAR, the CIGAR Regeneration module maintains counts of the number of matching bases, mismatching bases, inserted bases, and deleted bases. The CIGAR Regeneration module computes an alignment score as follows:

$$\text{Aero Alignment Score} = \left( \frac{\text{Matches}}{\text{Matches} + \text{Mismatches} + \text{Inserts} + \text{Deletions}} \right) * 100.0$$

While there is great diversity in alignment scoring, testing reveals that the Alignment Score provides good discrimination between well matching sequences and poorly matching sequences which are typically anticipated to be submitted to the system. Specifically, this score incorporates the balance of insertions and deletions with equal balance to lend a metric of overall comparability.

Alignment Score Filter

Alignment Records may have a low Alignment Score because of poor sample quality, large areas of genomic variability, or because an inappropriate reference sequence has been specified. An Alignment Filter module is implemented to identify Alignment Records whose Alignment Score fails to pass a user specified Alignment Score Cutoff. In these failing cases, the Alignment Filter module transfers the Alignment Record from the passing section in the Alignment Database to the failed section in the alignment database, and issue an appropriate warning. Users can then re-run their analysis with a lowered Alignment Score Cutoff if they feel this classification is inappropriate for their research.

Storage of Alignment Results

Alignment Records marked contained in the Good segment of the Alignment Database are ready for mixed-base variant analysis.

A Mechanism of Signal Processing in Sanger Base Sequencing

1 The Solution

Various embodiments described herein improves on the results of known algorithms that interpret electropherograms, and includes high-quality processes to accommodate many of the conditions identified above. A limitation of the previously-used algorithms is that it is "other sample agnostic." That is it is unable to take advantage of information included in other sequences. The embodiments described herein can fill this gap, first by providing a second order correction atop previous algorithms and also by using information from samples the user has grouped together to improve detection and accuracy.

Figure 4:
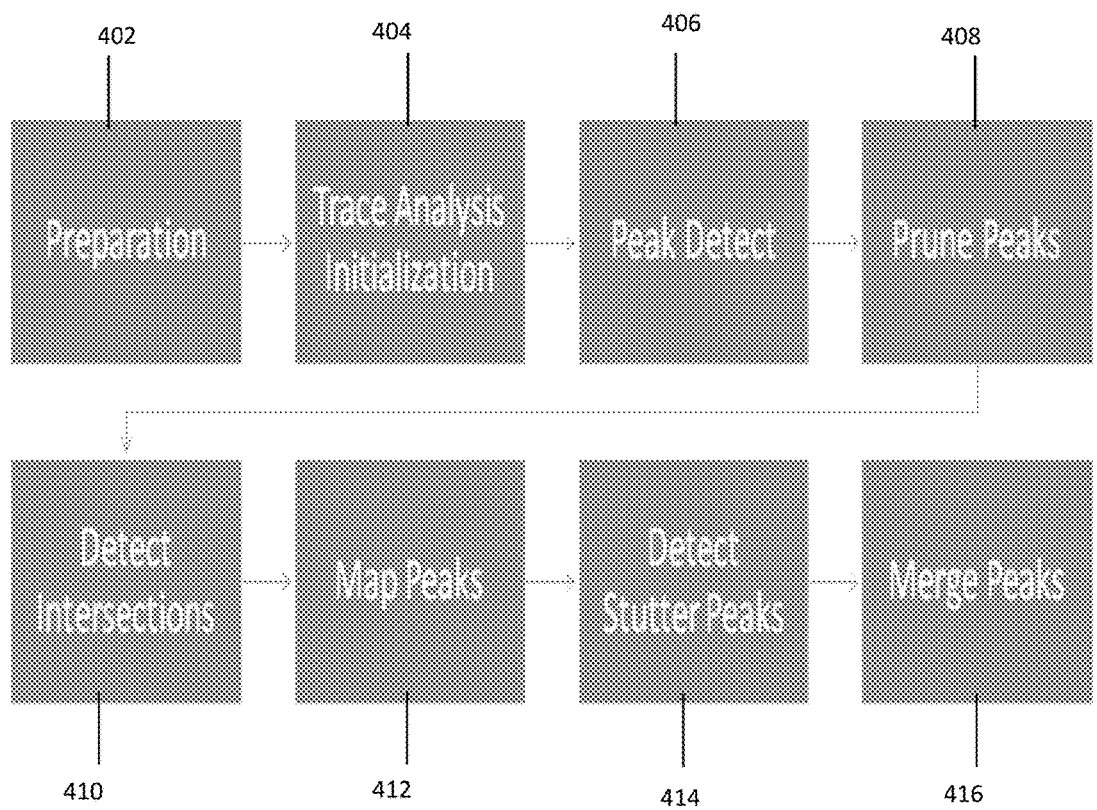
FIG. 4 illustrates a method of trace analysis according to various embodiments described herein.
Figure 6:
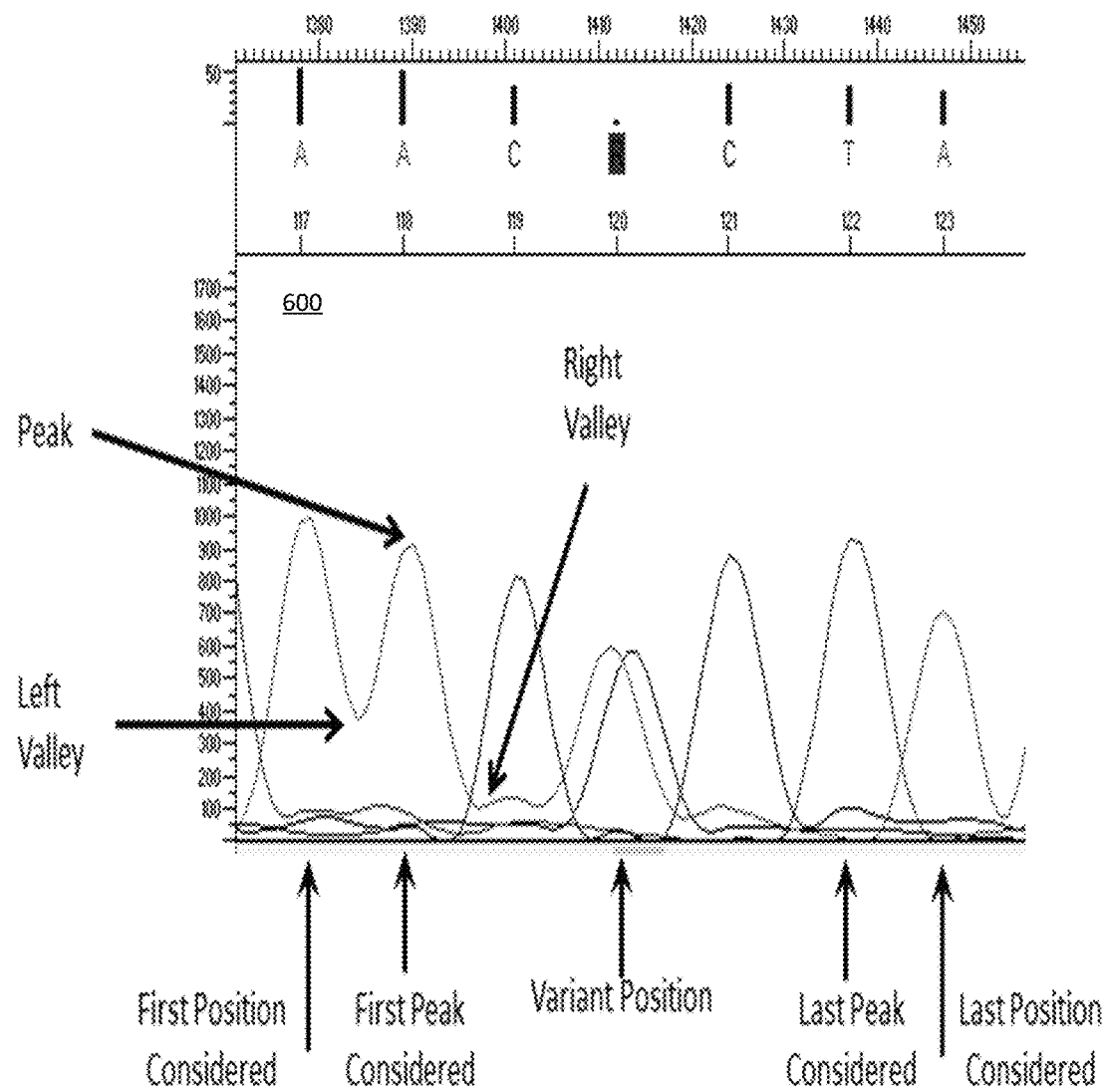
FIG. 6 illustrates a region of consideration according to various embodiments described herein.

The goal of the Trace Analysis module is to convert luminescent signals into biological signals, and to capture sufficient metrics to support scoring and validation which is shown in FIG. 4.

Reference Frames

The base call sequences are referenced in a number of different ways throughout the application. The reference frames depicted in FIG. 5 are defined by various embodiments described herein.

2 Trace Analysis Implementation

To prepare for Trace Analysis, the Electropherogram data is imported in step 402. The electropherogram data is received from the algorithm pipeline in a FASTA format but with proprietary formatted headers that indicate the contained data type. The Analyzed Trace Data is imported from the Electropherogram data for each of the four electropherogram channels. It additionally extracts the Peak Location data, the identification of the electropherogram sample from which the KB Caller produced the primary and secondary base call. Each channel of the Analyzed Trace Data is verified as well as the Peak Location data are present for each imported Query Sequence Record and that their length is consisted with the corresponding query sequence. Samples are rejected from further processing if they fail this validation.

The passing samples are added into the Query Sequence Database for subsequent access.

Next, the Alignment Database is accessed and each Alignment Record is reviewed to process its corresponding CIGAR. Each Insert, Deletion, and Mismatch CIGAR Operation is converted into a variant candidate described in a Variant Record. In cases where the CIGAR Operation indicates a length which is greater than 1 base pair, multiple Variant Records are produced for each base. The Variant Record describes the variant event, i.e. mismatch, insert, or deletion, includes the location of the variant in the reference sequence, and also in the query sequence. A variant string is additionally produced which indicates the bases involved in the variant, for example the fact that "A is substituted with T" would be captured. References to the Query Sequence Record, the Reference Sequence Record, as well as the Alignment Record are saved. These (candidate) Variant Records formulate the basis for subsequent Trace Analysis.

2.1 Trace Analysis Initialization

Figure 7:
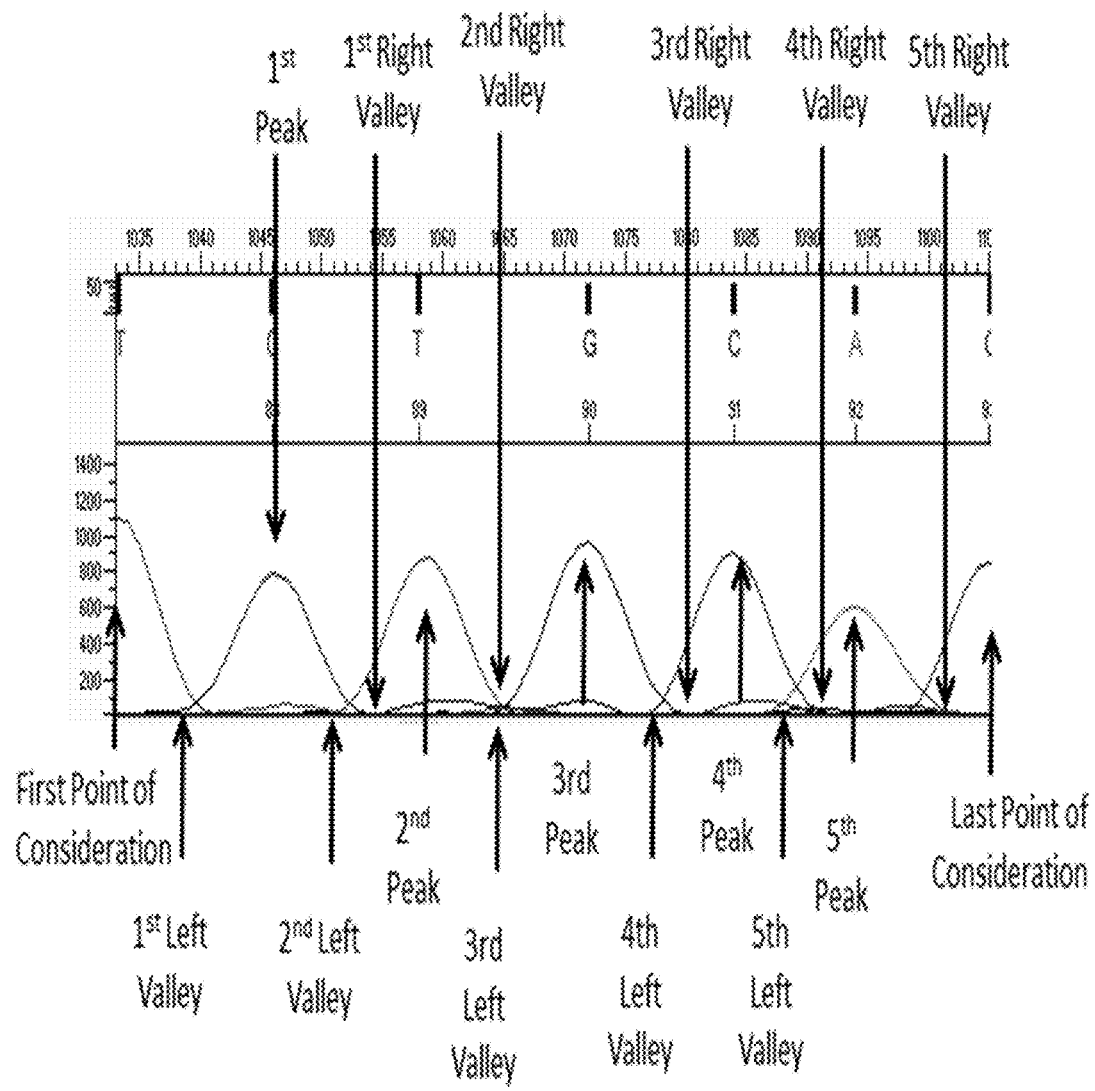
FIG. 7 illustrates another region of consideration according to various embodiments described herein.

Another feature according to various embodiments is execution of trace analysis in the mixed base variant validation/qualification of step 208 of FIG. 2. Trace analysis is initialized in step 404. Eliminating this non-productive analysis saves significant computation resources and provides near real-time results to the end-user. To accomplish this, as illustrated in Error! Reference source not found. 6, a region 600 in the forward reading query reference frame surrounding the point of interest is identified; that is, the base call position giving rise to the observation of mismatch or insertion, or the two base call positions giving rise to the observation of a deletion variant. To provide a statistical basis for certain calculations, the trace analysis is extended by two additional base call positions preceding and following the point of interest. Because the trace analysis begins with the detection of a valley of a peak, an additional base call position is added to both ends to define the region of the trace on the trace analysis is performed. Positioning either before the beginning of the electropherogram or exceeding beyond the end is avoided. To access data from the electropherogram, the range in the forward reading query reference frame is mapped to the original called-based reference frame, which depends on the original orientation of the sequence data along with the clear range locations. The called-base frame is then converted into the electropherogram reading frame with assistance of the Trace Call Positions (PLOC). FIG. 7 provides additional detail to this process. Analysis of a statistical number of electropherogram traces in the development of various embodiments described herein have assisted us in fine tuning the computation of these ranges to provide high accuracy and consistent results in defining consistent region for trace analysis.

2.2 Peak Detection

The goal of the Peak Detection module in step 406 of FIG. 4 is to convert the sequence of electropherogram data points into a discrete collection of signal observations (peaks.) A goal is to capture every meaningful inflection of the electropherogram with only cursory concern to validating the observations in the continuous form. Subsequent Trace Processing validates the signal observations as well as the biological significance, and we have only a cursory concern to validate the observations during the peak detection from the continuous form.

Figure 8:
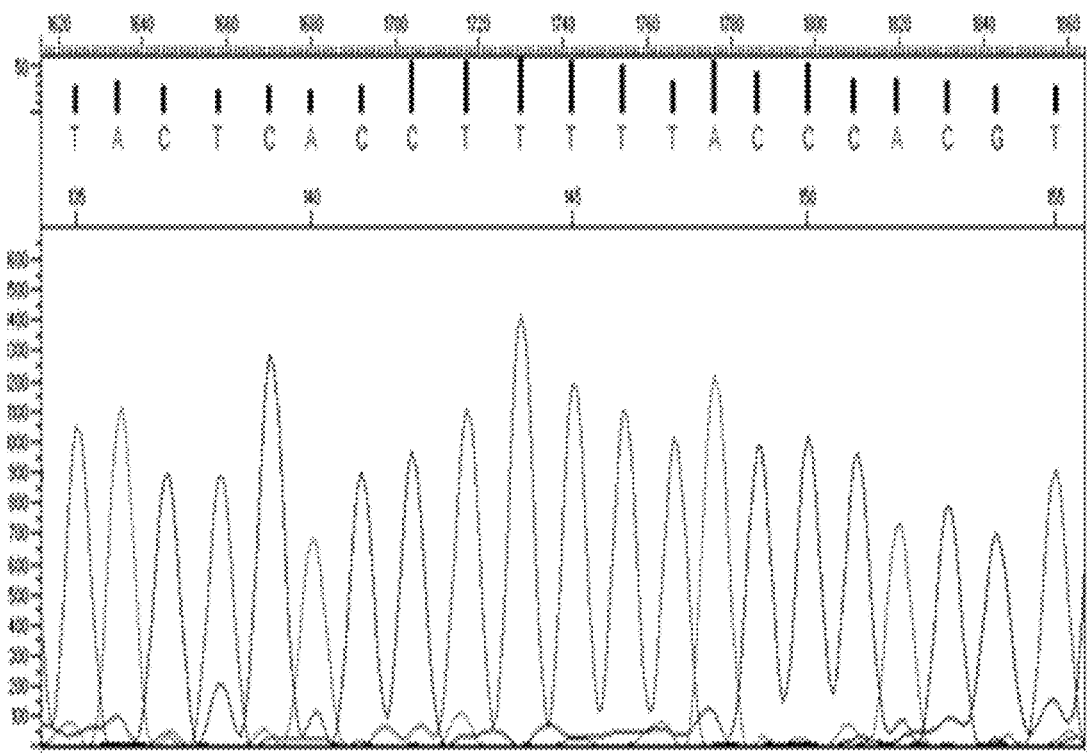
FIG. 8 illustrates an exemplary electropherogram according to various embodiments described herein.

The detection of peaks is complicated due to an irregular nature of the electropherogram peaks. As illustrated in FIG. 8, in a high-quality electropherogram, most peaks have a Gaussian shape with modulation that clearly rises above the noise floor and with little interference between the peaks. Note that the peaks are very evenly spaced and of nearly identical width. In this example, it is also likely that each peak has a single point of inflection where the height transitions from rising to falling, a single peak. In this case, the Peak Detection module will accurately detect and produce a sequence of peak objects. Each peak object describes the peaks apparent on the electropherogram, including the position, the width, the height the modulation, and sequence of these peaks.

Figure 9:
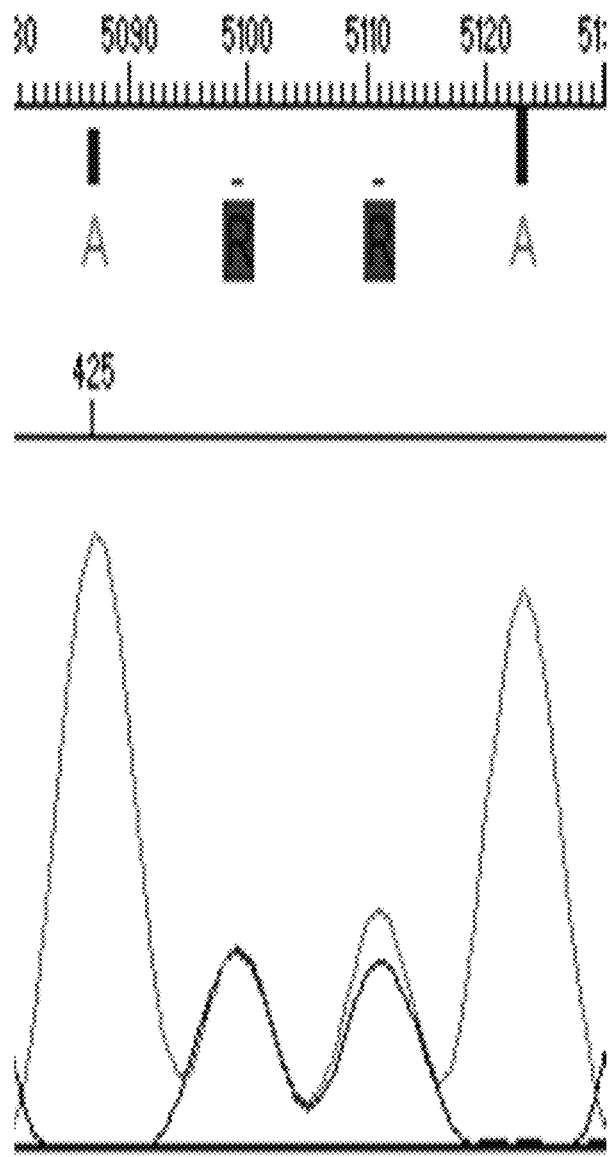
FIG. 9 illustrates an example of a mixed base report according to various embodiments described herein.

As illustrated in FIG. 9, electropherograms can also report mixed-base sequences. In this high-quality example, the two base modules are of nearly identical size and amplitude. There is no evident noise, and they are perfectly aligned. In this near perfect mixed-base example, the Peak Detection module of step 406 produces a list of peaks, including a peak for each of the green as well as black overlapping peaks (6 peaks in total for the example shown below.)

Figure 10:
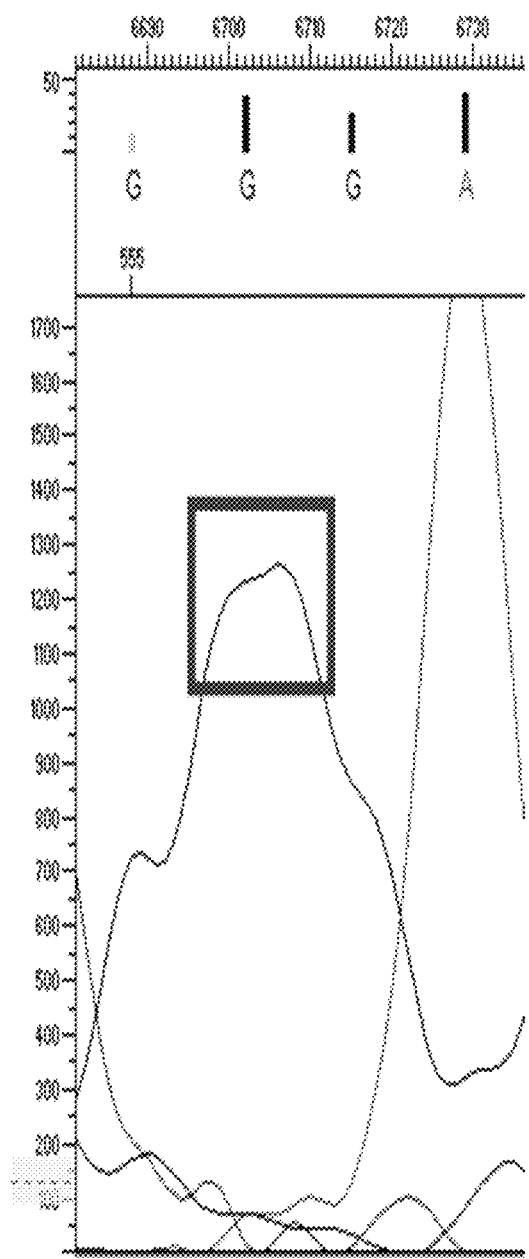
FIG. 10 illustrates an exemplary electropherogram characteristic that will be detected by the peak detection module according to various embodiments described herein.

FIG. 10 illustrates a case where the Peak Detection module routinely accommodates peaks which have a flattened portion, or a very nearly flat region on top, resulting in a clean inflection on its left and right side with no significant inflection between. Because of the high-precision required for the system, the Peak Detection module must report these peaks in a precise fashion.

Figure 11:
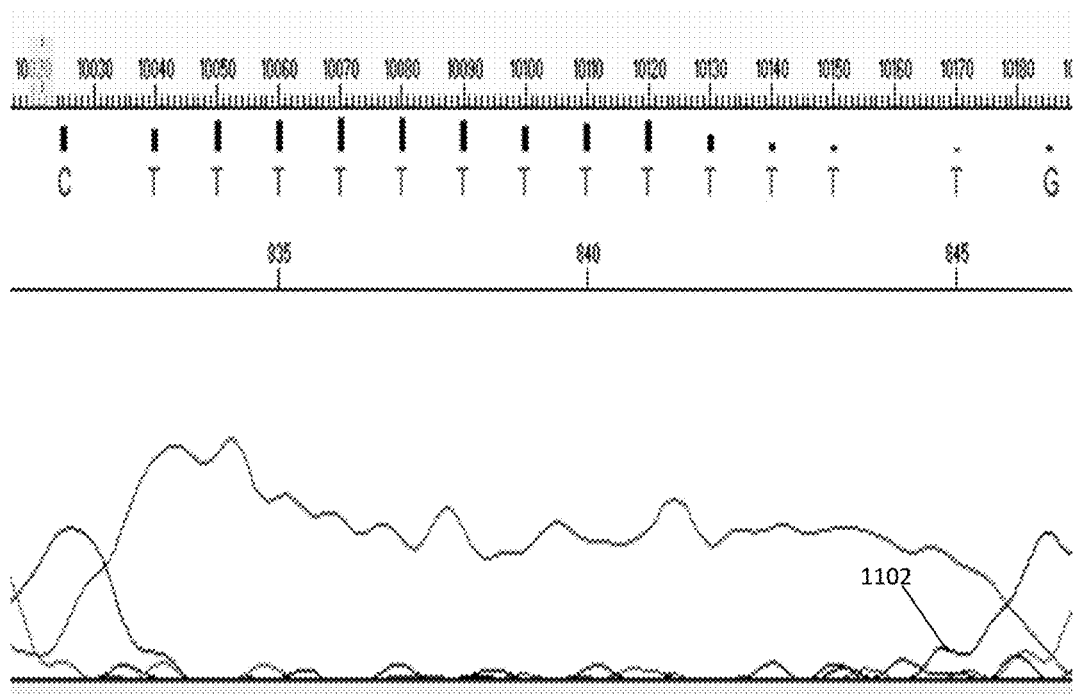
FIG. 11 illustrates yet another example of an electropherogram characteristic that will be detected by the peak detection module according to various embodiments described herein.

FIG. 11 provides an example of a signal (1102) which is biased high above the noise threshold but which has very low modulation. If these peaks were on the noise floor, they would compete unfavorably with noise. However, as biased to a high amplitude, these low-modulation peaks are generally valid biological signals. The Peak Detection module of step 406 will detect and produce peak objects in this case.

Figure 12:
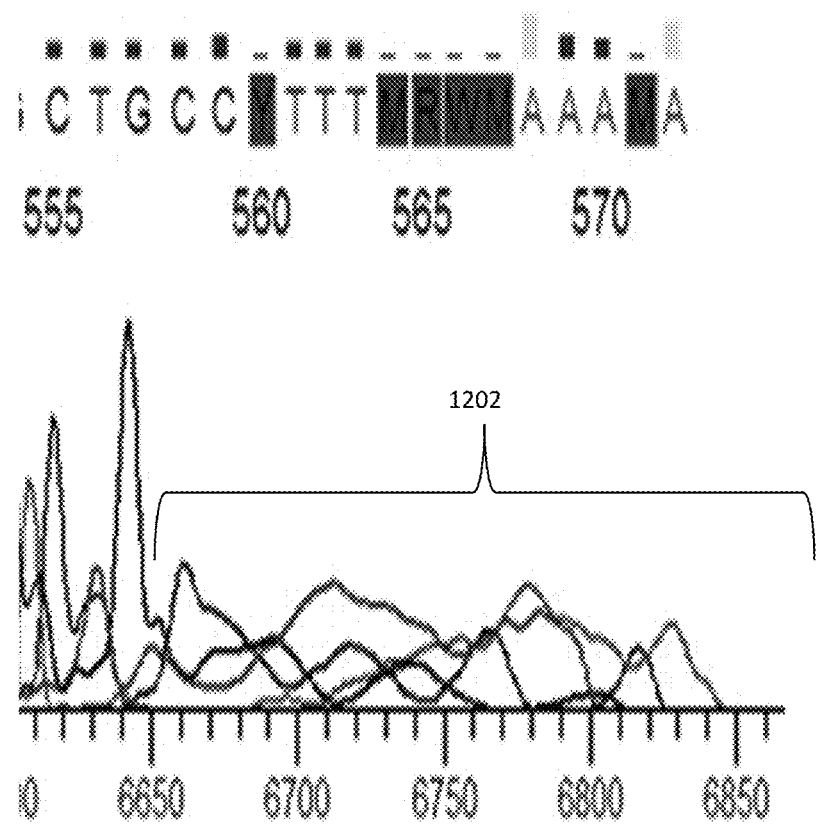
FIG. 12 illustrates yet another example of an electropherogram characteristic that will be detected by the peak detection module according to various embodiments described herein.

FIG. 12 illustrates the region 1202 that signal quality is typically low at the ends of the electropherogram. The peaks become diffuse and mixed. Typically this data is removed in quality trimming prior to processing. However, in some cases residual low-quality bases will remain. This is a well characterized phenomena. In this case, the Peak Detection module of step 406 may produce many peaks based on the various tuning parameters. Some of these peaks may represent valid biological signals while some peaks may represent signal noise and be subsequently rejected.

Figure 13:
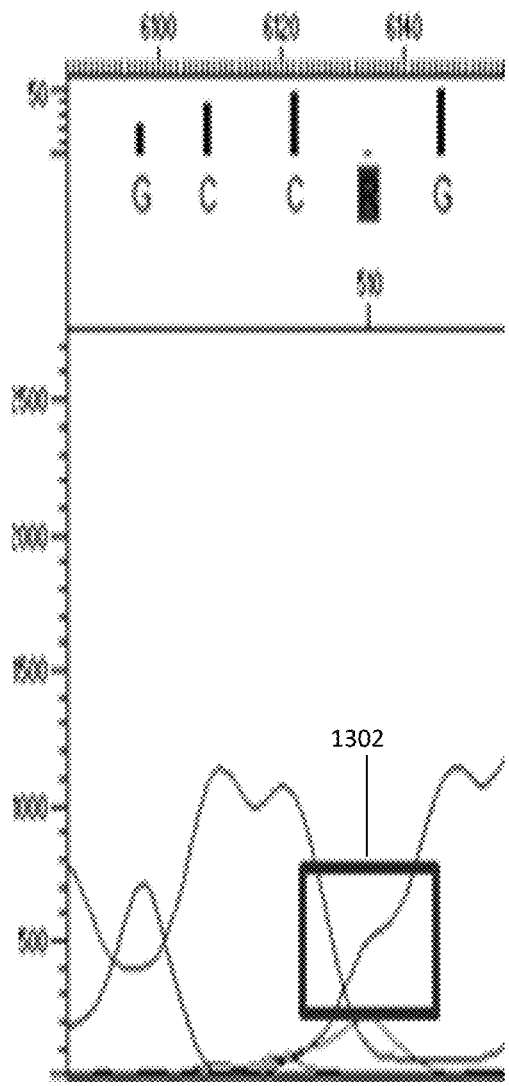
FIG. 13 illustrates yet another example of an electropherogram characteristic that will be detected by the peak detection module according to various embodiments described herein.
Figure 14:
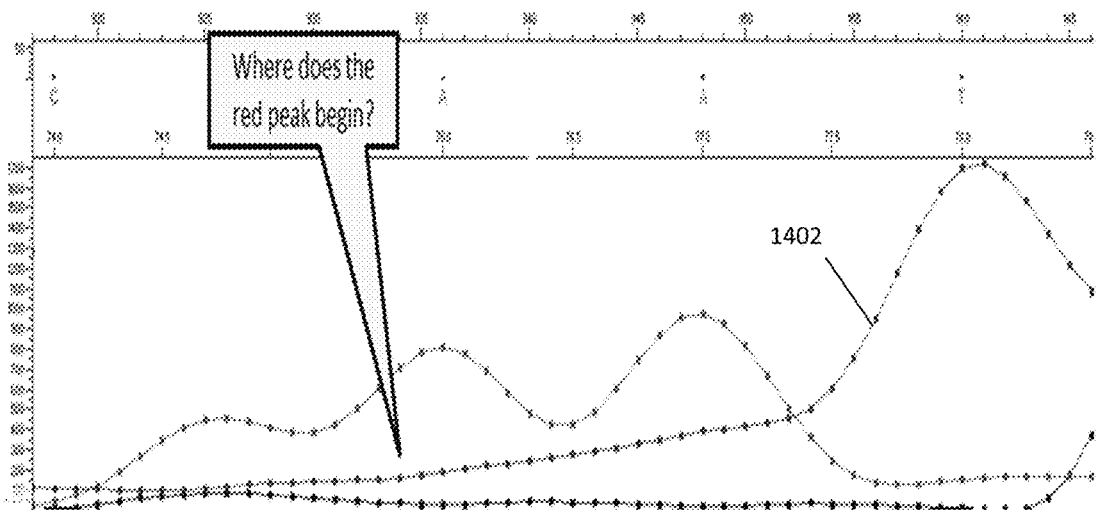
FIG. 14 illustrates yet another example of an electropherogram characteristic that will be detected by the peak detection module according to various embodiments described herein.
Figure 15:
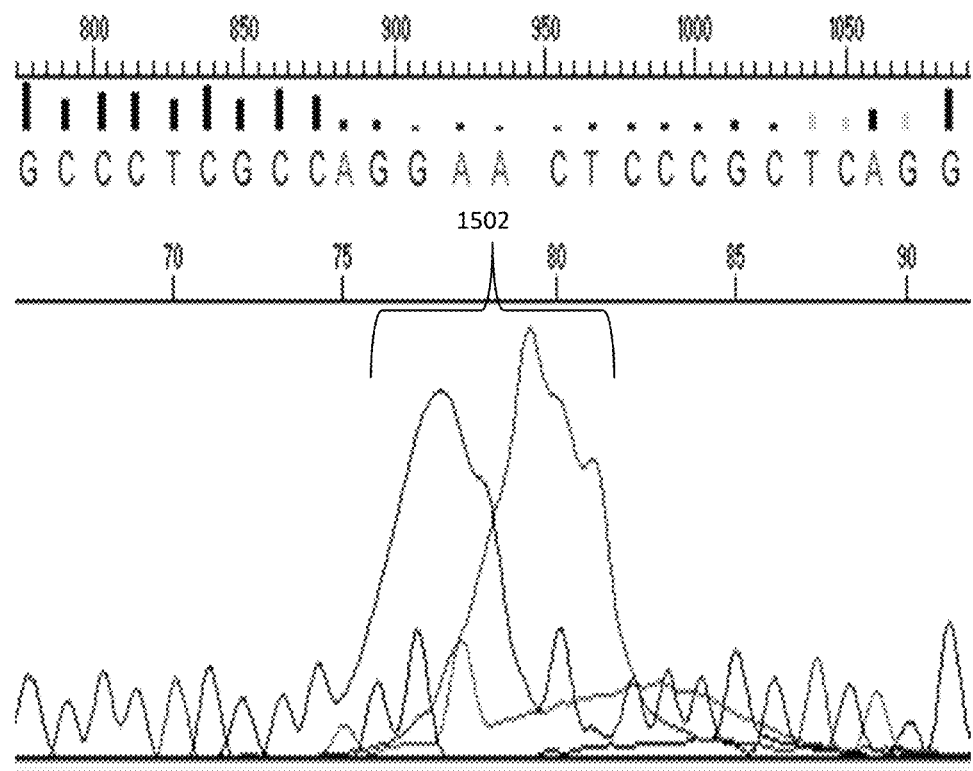
FIG. 15 illustrates yet another example of an electropherogram characteristic that will be detected by the peak detection module according to various embodiments described herein.

FIG. 13 depicts another phenomena that exists is shoulder-peaks in region 1302, in which two peaks are characterized by the first rising to a plateau, but not descending in a valley, and followed immediately by a rise to a taller peak. The same kind of shoulder-peak can occur on the falling size, when a tall peak descends to a plateau followed by a descent to the noise floor. In this case the Peak Detection module detects the shoulder peak condition and produce two peaks. Parameters determine the limits for this detection.

Error! Reference source not found. 14 shows an example of an extended valley with a slowly rising, low slope which interferes with two proceeding peaks before rising to a legitimate peak itself in trace 1402. This slope, which begins in the noise region, rises to the level of a mixed base and could inadvertently trigger a false mixed-base call by KB caller.

Error! Reference source not found. 15 provides an example of a clean electropherogram with a glitch resulting in two exaggerated peaks (in region 1502). An additional elongated peak (green) lies below those two. These irregularities are sometimes referred to as dye blobs. The true positive inflection is preserved in these but not produce false positive calls.

Figure 16:
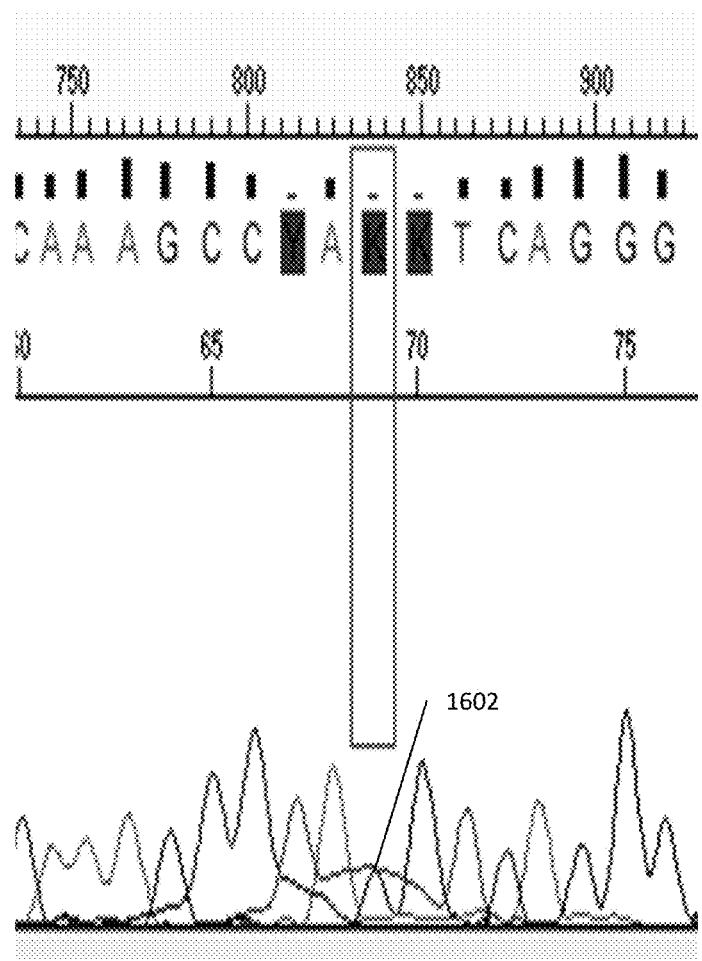
FIG. 16 illustrates yet another example of an electropherogram characteristic that will be detected by the peak detection module according to various embodiments described herein.

FIG. 16 shows a case similar to that above, but having an irregular elongated peak (1602). This peak spans three well-formed peaks and results in KB Caller producing two mixed base calls. The Peak Detection module should detect this peak, but enable its subsequent removal.

The Peak Detection module processes each Variant Record from the Variant Record Database to detect peaks, which represent detection of a particular DNA base in a specific relative sequence from the sampled electropherogram data. Subsequent processing during Trace Analysis performs additional validation of these peaks, and they undergo significant subsequent process before they are declared valid biological observations of variance to the reference sequence.

Figure 17:
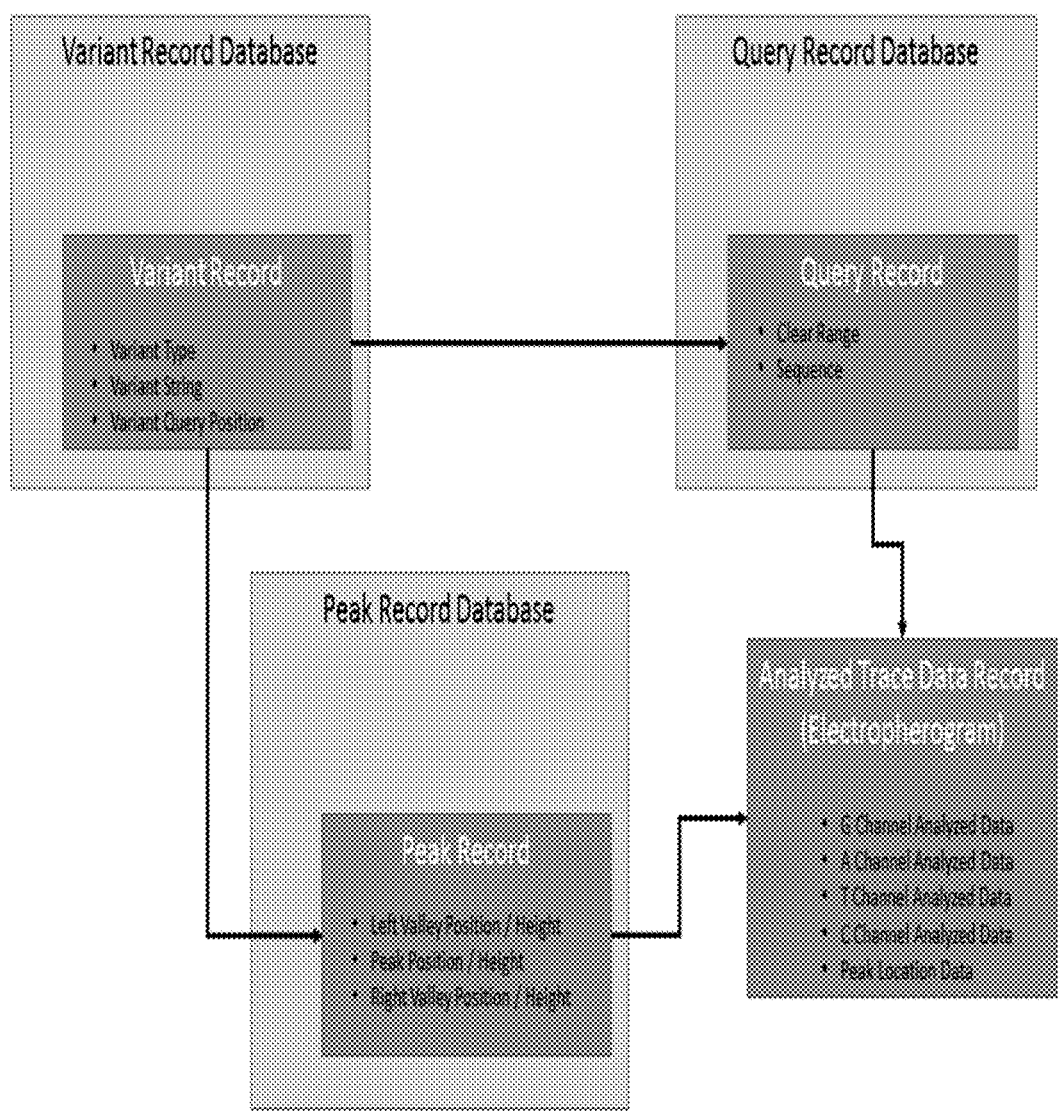
FIG. 17 illustrates an exemplary peak detection system according to various embodiments described herein.

FIG. 17 provides an overview of the data organization which supports the Peak Detection module. For each Variant Record (variant candidate), the Peak Detection module processes the electropherogram data associated with the variant candidate's Query Record. Each of the four channels (Analyzed Trace Data) is processed independently, considering each data point through the region of the electropherogram identified during Trace Analysis Initialization, described above. During processing the Peak Detection module produces Peak Records and adds these into a Peak Collection database that is associated with the considered Variant Record. The Peak Detection module populates the Peak Record with the following basic information: trace channel on which the peak was identified, corresponding to the DNA bases of G, A, T, and C, Left Valley position and height, Peak position and height, and Right Valley position and height.

The Peak Detection module characterizes a peak as having a left and right valley and a peak. The Peak Detection module implements a state machine to facilitate detection with the transitions: Seeking Left Valley, Seeking Left Peak, Seeking Right Peak, and Seeking Right Valley.

Figure 18:
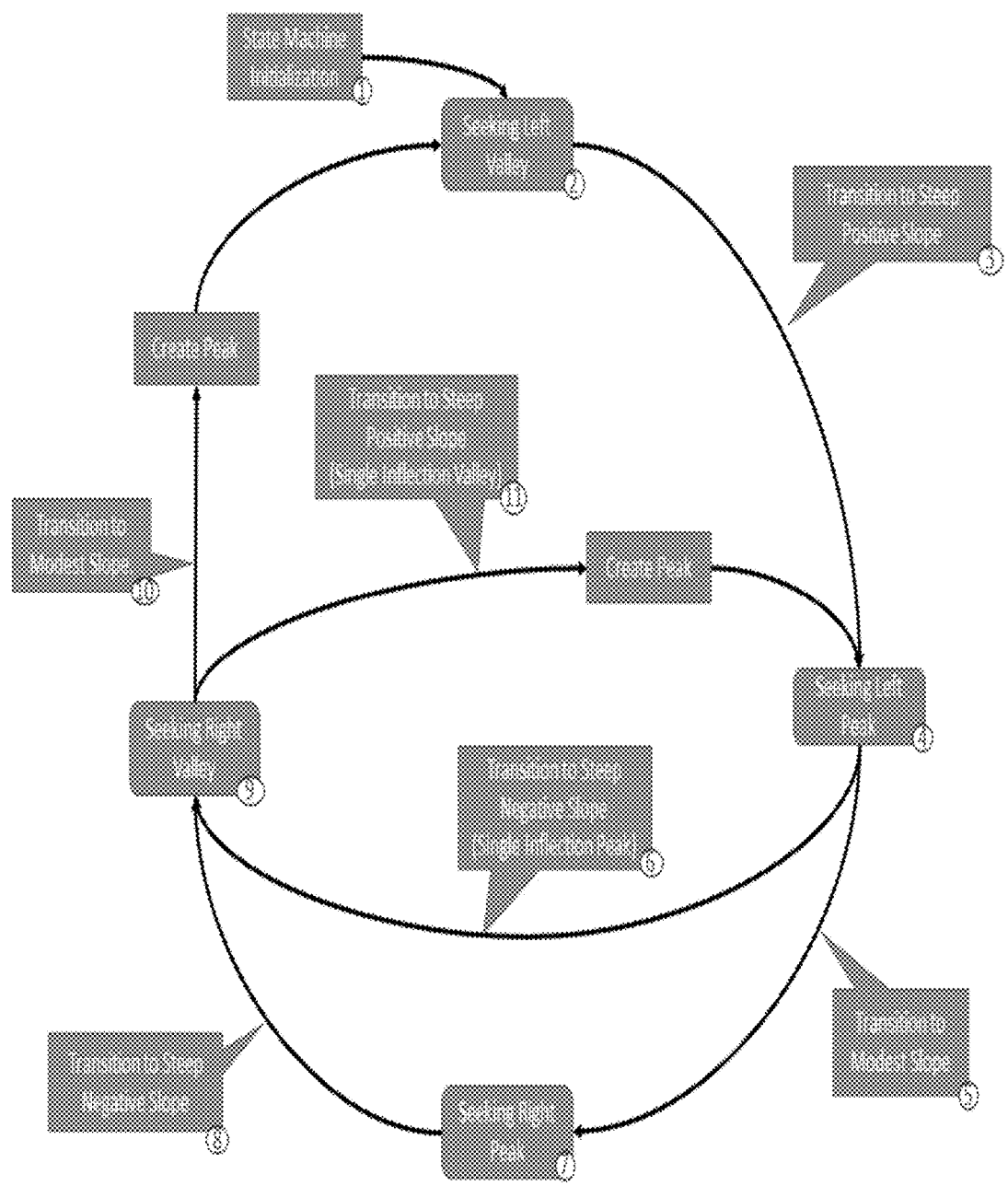
FIG. 18 illustrates an example of a peak detection method according to various embodiments described herein.

FIG. 18 illustrates the detection of non-shoulder peaks.

1.) Upon the initial entry into each channel, the Peak Detection module initializes various state variables in order to avoid an initial state transition when processing the first trace point. The Peak Detection Module sets the machine into the Seeking Left Valley state.

2.) The Peak Detection module will sequentially consider analyzed data points and calculate the slope as the difference of the current and last data point's height. It will not change the state of the machine from Seeking Left Valley state so long as the slope remains moderate and neither steeply positive or steeply negative.

3.) If the Peak Detection module encounters a steep positive slope it will set the machine into the Seeking Left Peak state, and remember the position and height of the last considered data point as the Left Valley position and height.

4.) The Peak Detection module will remain in the Seeking Left Peak state while considering data points remain steeply positive.
5.) If the Peak Detection module encounters a reduction of the slope from steeply positive to moderately positive, but more positive than steeply negative, then the Peak Detection module will set the machine to the Seeking Right Peak state and remember the Left Peak height and position as the taller of the current or last data point's height and position.
6.) If instead the Peak Detection module encounters a steeply negative slope, it will set the machine into the Seeking Right Valley state and remember the Left Peak height and position as well as the Right Peak height and position as the taller of the current or previous data point's height and position.
7.) The Peak Detection module remains in the Seeking Right Peak state while the slope of the considered data points is more positive than steeply negative.
8.) If the Peak Detection module encounters a transition of the slope to steeply negative, then the Peak Detection module will set the Seeking Right Valley state and store the Right Peak height and position as the taller of the current or last data point's height and position.
9.) The Peak Detection module remains in the Seeking Right Valley state while the slope of the considered data points is steeply negative.
10.) If the Peak Detection module encounters a moderate slope more positive than steeply negative and not as positive as steeply positive, then the Peak Detection module will set the machine to the Seeking Right Valley state and remember the Right Valley height and position as the current data point's height and position. The Peak Detection module will proceed to create a Peak Record with the remembered Left Valley height and position, the Peak height and position, being the average of the Left Peak height and position and the Right Peak height and position, and with the Right Valley height and position. The Peak Detection module will add the new Peak Record to the Peak Record Database, associated with the variant candidate under consideration.
11.) If instead, the Peak Detection module encounters a steeply positive slope, then the Peak Detection module will set the machine to the Seeking Left Peak state and remember the Right Valley height and position as the current data point's height and position. The Peak Detection module proceeds to create a Peak Record and add it to the Peak Record Database as previously described. Additionally, the Peak Detection module sets the Left Valley height and position to the Right Valley's height and position.

The Peak Detection module continues to process data points for the four traces, compiling Peak Records into the Peak Record Database until the range described during Trace Analysis Initialization (Section Trace Analysis Initialization2.1) is consumed.

Figure 19:
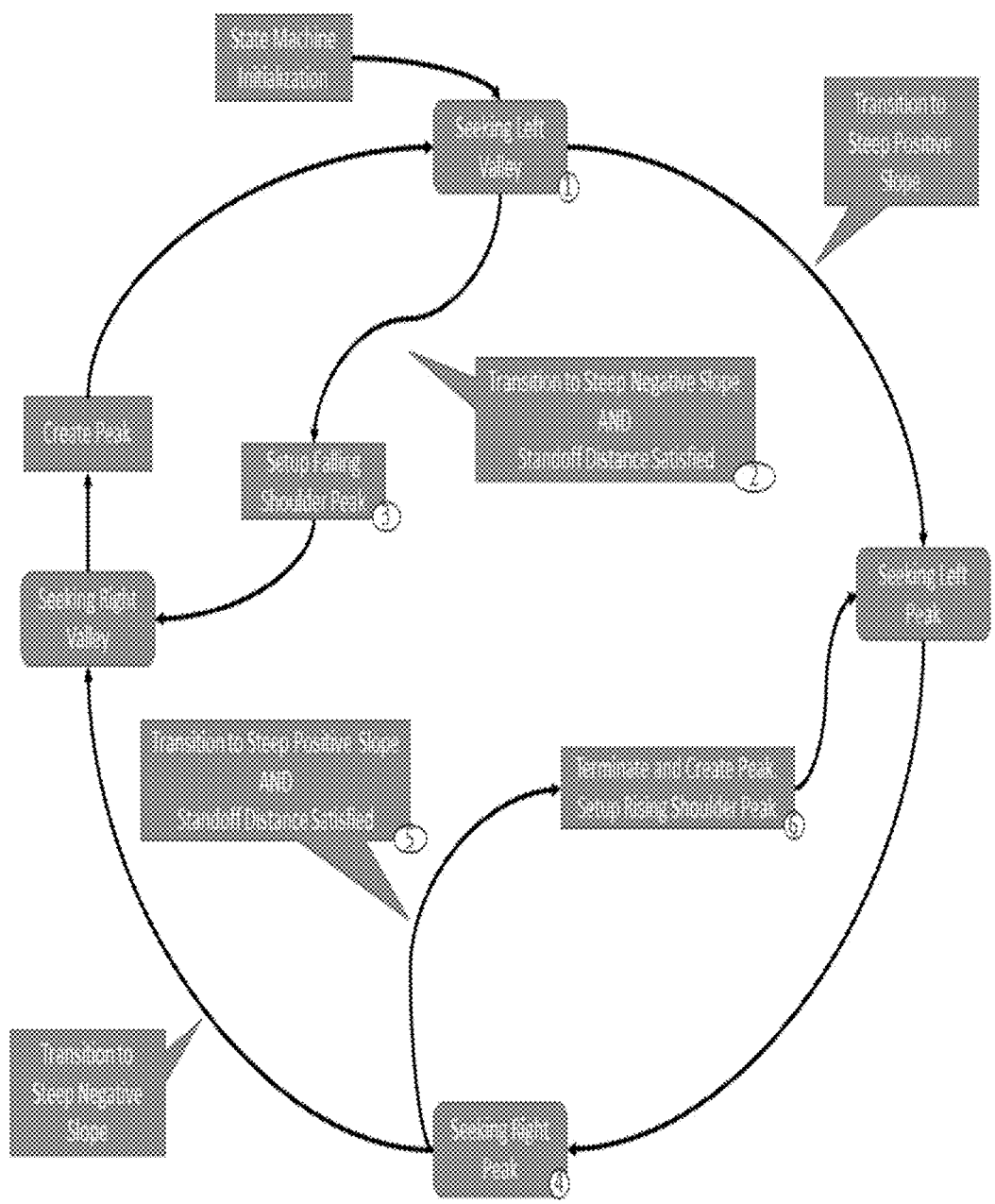
FIG. 19 illustrates another example of a peak detection method according to various embodiments described herein.
Figure 20:
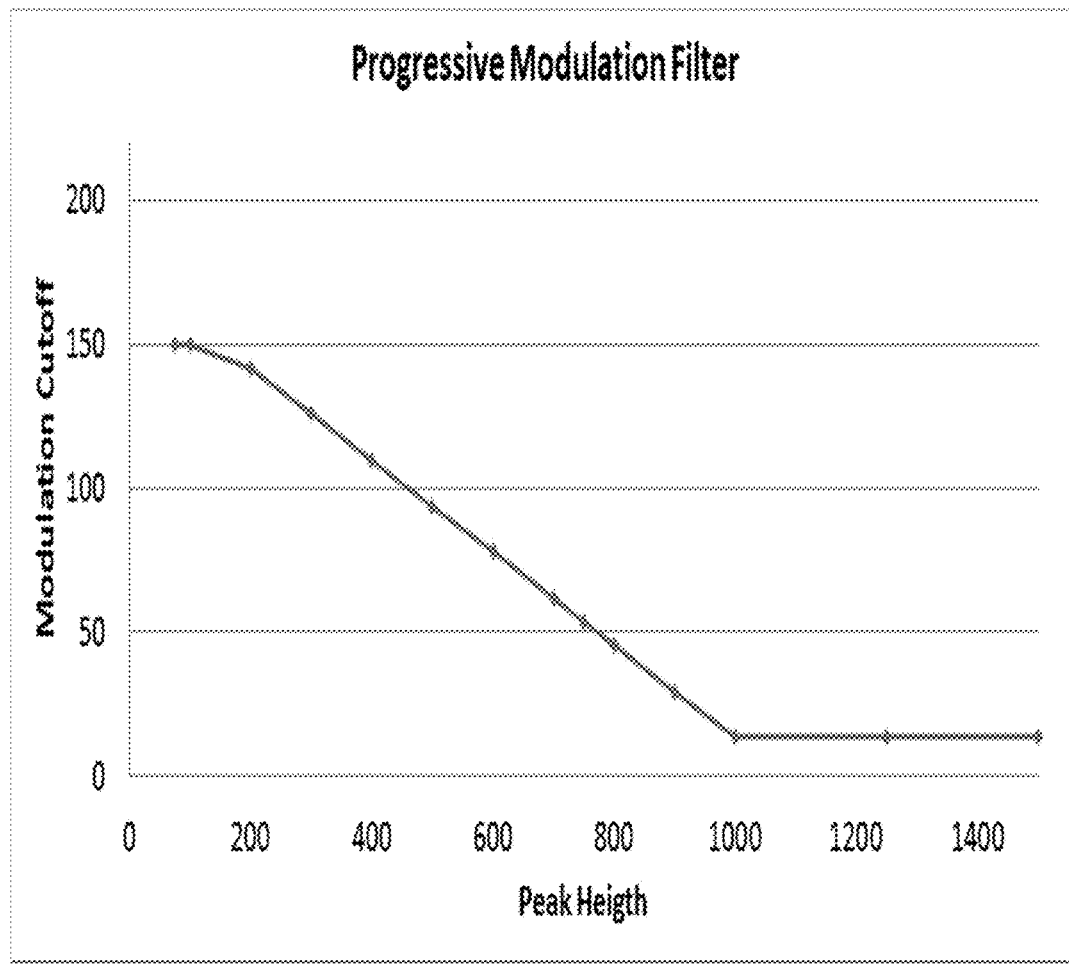
FIG. 20 illustrates an exemplary progressive modulation filter according to various embodiments described herein.

The Peak Detection module additionally implements detection for shoulder peaks as illustrated in FIG. 13. Shoulder peaks "add-on" to a currently building peak without having a descent to a valley. FIG. 19 illustrates the state machine diagram for detection of shoulder peaks.

1.) While the machine is in the Seeking Left Valley state, the Peak Detection module sequentially considers analyzed data points and calculate the slope as the difference of the current and last data points' heights. It will not change the state of the machine from Seeking Left Valley state so long as the slope remains moderate and is neither steeply positive nor steeply negative.
2.) If the Peak Detection module encounters a steep negative slope, the distance from the last peak position and also the height of the current declining data point are evaluated. If the distance from the last peak is below a minimum, or the current data point's height is too low, the Peak Detection module leaves the machine in the Seeking Left Valley state.
3.) Otherwise, the Peak Detection module computes the Left Valley position as the greater of the last Right Valley position and the current position less the minimum detection distant. The Left Valley height is computed from the actual trace height at the computed Left Valley Position. The Left Peak height and position and the Right Peak is stored as the current position. Finally, the Peak Detection module sets the machine to the Seeking Right Valley state.
4.) While the machine is in the Seeking Right Peak state, the Peak Detection module sequentially considers analyzed data points and calculates the slope as the difference of the current and last data points' heights. The state of the machine from Seeking Right Peak state does not change so long as the slope remains moderate and is neither steeply positive nor steeply negative.
5.) If the Peak Detection module encounters a steep positive slope, the distance from the last Left Peak position and also the height of the current data point are evaluated. If the distance from the last Left Peak is below a minimum, or the current data point's height is too low, the Peak Detection module leaves the machine in the Seeking Right Peak state.
6.) Otherwise, the Peak Detection module stores the Right Peak height and position as equal to the Left Peak height and position, and stores the Right Valley position as the current data point's position and the Right Valley height as the lower of the Right Peak's height and the current data point's height. The Peak Detection module creates a new Peak Record based on the Left Valley, the Peak, and the Right Valley and adds it to the Peak Record Database. A new peak is stored by storing the Left Valley position as the greater of the Right Valley position and the current position less the minimum detection distance. Finally the Peak Detection module sets the machine to the Seek Left Peak state.

2.3 Peak Pruning

The purpose of peak pruning (step 408 in FIG. 4) is to eliminate signal observations (peaks) which fail validation certain metrics. This process provides a first-pass filter on the interpretation of the continuous data into discrete observations on common signal properties. The Peak Pruning Module considers all the peaks produced by the Peak Detection module as follows:

2.3.1 Amplitude Filter

The Peak Pruning module applies a minimum height filter to all peaks. Peaks whose height falls below the minimum level are marked for deletion and receive no further consideration. The threshold for this filter is determined by analyzing a large set of expertly curated data which included broad diversity regarding experimental design, instrumentation, and data quality. According to various embodiments, a threshold is selected so that no legitimate signal is excluded but rather that signals may be distinguished from background noise.

2.3.2 Progressive Modulation Filter

To distinguish signals from noise, a filter is imposed on the degree of modulation for a peak to be considered a valid signal. Error! Reference source not found. 11 illustrates a phenomena which is encountered where a bias boosts the height of a signal peak and also the signal valley. The signal, if occurring on the signal floor would have insufficient modulation to rise above the noise. However, at the higher amplitude there is no competition for the noise and the modulation stringency can be relaxed. The Peak Pruning module applies a progressive modulation filter which is tuned so that signals require greater modulation when they have low amplitude and less modulation when they have greater amplitude.

Error! Reference source not found. 20 describes the design of the progressive modulation filter. The peak height determines the modulation cutoff; that is the modulation below which the peak will be rejected.

The signal modulation module is designed to normalize non Gaussian peaks, to eliminate the effect of long leading and trailing tails, and to provide a degree of algorithmic normalization to shoulder peaks. The modulation is computed as follows:
1.) For the computation of modulation, the peak is considered as a left-side right triangle and a right-side right triangle.
2.) The effective left-side valley position is the larger of the detected left-side valley position and the peak position, less the nominal half-peak width.
3.) The effective right-side valley position is the smaller of the detected right-side valley position and the peak position plus the nominal half-peak width.
4.) The effective left-side valley height is the actual trace height at the left-side valley position. The effective left-side valley height is further limited to the height of the peak height.
5.) The effective right-side valley height is the actual trace height at the right-side valley position. The effective right-side valley height is further limited to the height of the peak height.
6.) The effective valley height is the less of the effective left-side valley height and the effective right-side valley height.
7.) The modulation is the peak heights less the effective valley height.

In application of the progressive modulation filters:
1.) The height of the peak is computed and compared to the progressive modulation definition (Error! Reference source not found. 20).
2.) If the height of the peak exceeds the peak modulation ceiling, the peak is considered to have passed the peak modulation filter.
3.) Otherwise, if the height of the peak falls below the minimum peak modulation height, the peak is considered to have failed the peak modulation filter.
4.) Otherwise, the modulation of the peak is computed as described above.
5.) A modulation score is computed as the ration of the peak modulation and the Min Peak Modulation as described above.
6.) For cases where the ratio is greater than one, the peak is considered as passing the progressive peak modulation filter. In cases where the ratio is less than one the peak is considered to have failed the peak modulation filter, however the peak is not marked for deletion, but is rather assigned a Low Modulation flag is set on the peak and the modulation score is recorded for subsequent consideration during variant scoring.

2.3.3 Minimum Peak Width Filter

Peaks which are detected with abnormally narrow width do not convey biological information and will receive no further consideration. The Prune Peak module:
1.) Compute the width of the peak as the detected right valley position less the detected left valley position.
2.) If the width falls below the minimum width threshold, the peak is marked for deletion 2.3.4 Excessive Peak Width Filter Peaks may be detected with excessive width do not convey biological information and will receive no further considerations. The Prune Peak module:
1.) Compute the width of the peak as described above.
2.) If the width exceeds a maximum width threshold, the peak is marked for deletion.

2.4 Intersection Detection and Calculation

With reference back to FIG. 4, the Intersection Detection and Calculation module in step 410 identifies the intersection, or overlap, of adjacent peaks. The computation of intersection is critical in detection of mixed-base peaks and also of interference. Further, the intersection is used as a critical factor in determining variant discrimination and confidence scoring. This process is uniquely implemented in the methods and systems described herein to be efficiently executed and produce highly accurate and unbiased results. The computation of intersection consists of two modules, detection of intersection and computation of the intersection. The detection of intersections is performed in an optimized fashion, using two indexes which slide through the data points to minimizes the total number of computations involved. The computation of intersection follows detection and is performed based on the detected intersections. Because peaks may be asymmetric, particularly in the case of shoulder peaks, the valleys of the primary and each subordinate peak are normalized in a fashion to provide the fairest numeric benefit to asymmetric peaks prior to computation of intersection. Additionally, to normalize comparisons of peaks resting on the noise floor to those which have an amplitude bias, the computation of intersection only considers the modulated portion of the trace. Finally, irregularities can occur such as the subordinate being larger than the primary peak, or traces dipping below the normalized valley are addressed to prevent inaccurate computation of intersection.

2.4.1 Intersection Detection

The Intersection Detection and Calculation module detects intersections between peaks as follows:
1.) The Intersection Detection and Calculation module is invoked to consider the Peak Database for each Variant Record in turn.
2.) For each Peak Database, the Intersection Detection module orders the peaks in order of ascending Left Valley position.
3.) The Intersection Detection and Calculation module maintains two indexes, one for the primary peak and one for secondary peaks. The primary peak is the peak for which intersections are being identified. The secondary peaks are the peaks which are being evaluated for intersection.
4.) The Intersection Detection and Calculation module checks to determine if the Right Valley of the secondary intersects with the Left Valley of the Primary, and if the overlap is greater than the minimum overlap, then a reference to the secondary peak is added as a subordinate in the primary Peak Record.
5.) The Intersection Detection and Calculation module checks to determine if the Left Valley of the secondary intersects with the Right Valley of the Primary, and if the overlap is greater than the minimum overlap, then a reference to the secondary peak is added as a subordinate in the primary Peak Record.

6.) The Intersection Detection and Calculation module remembers the last productive position of the secondary index and updates it when the secondary peak falls fully behind the primary peak in order to avoid performance of unnecessary comparisons or to miss potential intersections.

2.4.2 Intersection Calculation

The computation of intersection follows the detection and is computed as follows:

1.) For the computation of the intersection, compute the primary peak's effective valley height:

Effective Left Valley Position=max(Detected Left Valley Position,Detected Peak Position−Half Peak Width Constant)

Effective Right Valley Position=min(Detected Right Valley Position,Detected Peak Position+Half-Peak Width Constant)

Effective Left Valley Height =min(Trace Height[Effective Left Valley Position],Detected Peak Height)

Effective Right Valley Height =min(Trace Height [Effective Right Valley Position],Detected Peak Height)

Effective Valley Height=min(Effective Left Valley Height,Effective Right Valley Height)

2.) For every trace data point (Trace Height) between the Effective Left Valley Position and the Effective Right Valley Position. For each point compute:

Effective Primary Height[$i$]=max(0,Primary Trace Height[$i$]−Effective Valley Height)

3.) Compute the primary peak's area:

Primary Peak Area=ΣEffective Primary Height[$i$]

4.) For every trace data point between the Effective Left Valley Position and the Effective Right Valley Position (j), and for each subordinate peak (i), compute:

Effective Subordinate Height[$i,j$]=min(max(0,Subordinate Trace Height[$i,ji$]−Effective Valley Height),Effective Primary Height[$i$])

5.) For every trace data point between the Effective Left Valley Position and the Effective Right Valley Position (j), and for each subordinate peak (i), compute:

Subordinate Intersection[$i,j$]=min(Effective Subordinate Height[$i,j$],Effective Primary Height[$j$])

6.) For every trace data point between the Effective Left Valley Position and the Effective Right Valley Position (j), compute:

Largest Subordinate Intersection[$j$]=max(Subordinate Intersection[0],Subordinate Intersection[1] . . . Subordinate Intersection[$n$])

7.) Compute the overlap area as:

$$\text{Overlap Area} = \sum_{\text{Effective Left Valley Position}}^{\text{Effective Right Valley Position}} \text{Largest Subordinate Intersection}[f]$$

2.5 Map Peaks

The purpose of the Map Peaks module in step 412 of FIG. 4 is to align peak observations with the base call produced by KB Caller. Mapping the trace analysis observations with the KB Caller results is critical because the KB Caller produces the basic hypothesis for variants, and the trace analysis reinforces or refutes that hypothesis. Incorrect mapping will generally result in reinforcing an invalid base call or refuting a valid base call. With high-quality traces that have regular well-formed peaks, a trivial implementation might adequate, however the analysis of traces which have a high level of a repeated bases, or with highly degraded signals in the trace ends, there is a significant opportunity to encounter peaks which are out of cadence, and also multiple peaks that compete for the same base call position. A worst case occurs when a peak falls equally between two base call positions. Analysis of a large highly curated data set has revealed that the spacing between peaks is regular within a certain range of values, and this knowledge is used in the mechanization of the mapping function described below.

Figure 21:
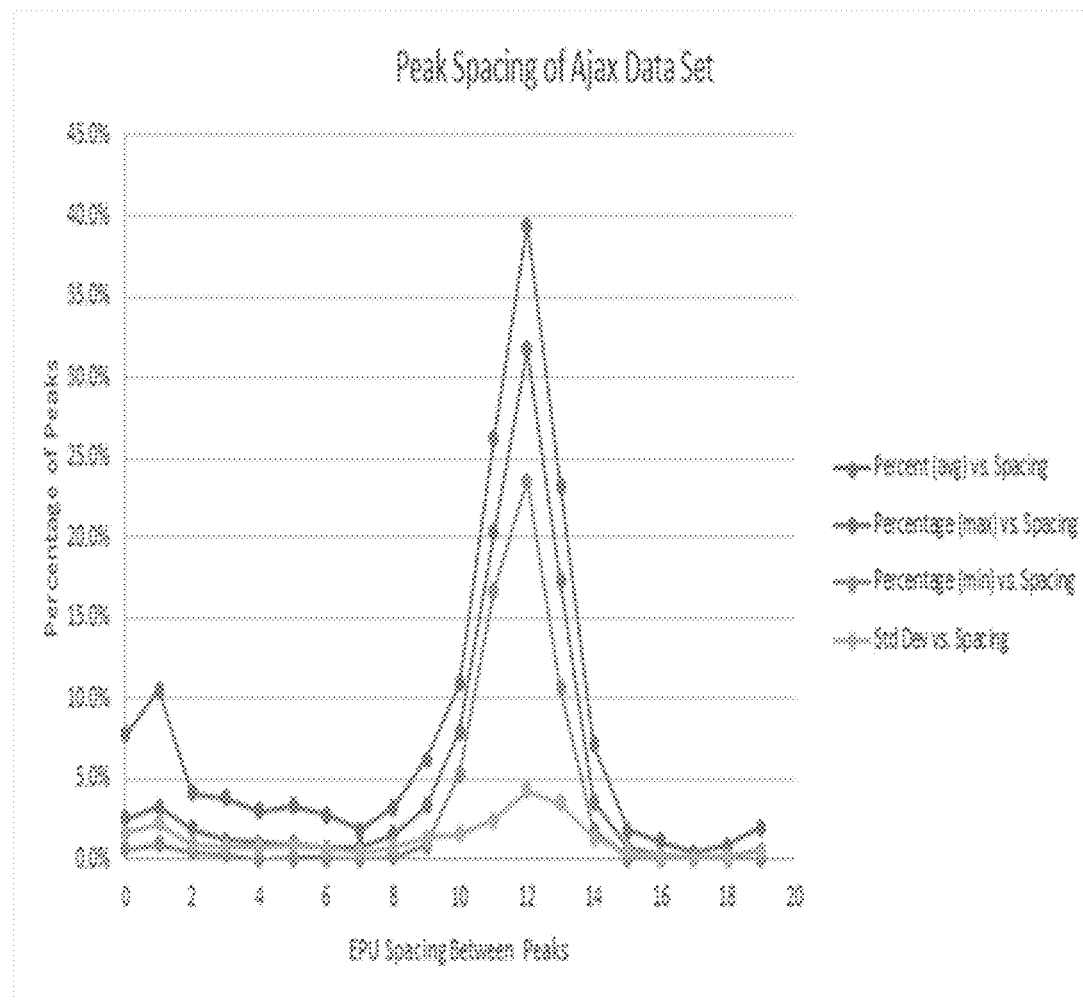
FIG. 21 illustrates an example of a mapping peaks function according to various embodiments described herein.

The mapping of peaks to base call query position is performed as follows, and is illustrated in FIG. 21:

1.) Order the peaks in ascending order based on the Left Valley position.

2.) For each Peak, consider each Query Position in the query range defined during Trace Analysis Initialization (Section 2.1), from first to last.

3.) Convert the Query Position from the Forward Reading reference frame into an index in Base Call coordinates for forward reading samples as follows:

Base Call Index=Query Position+Clear Range Start Position and for reverse reading samples Base Call Index=Query Length−1−Query Position+ Clear Range Start Position 4.) Obtain the Trace Coordinate for the considered query position from the Trace Call Position (PLOC) using the Base Call Index.

5.) Compute the Mapping Distance as the difference between the Trace Coordinate identified from the Query Position and the Peak Position determined during Peak Detection (Section 2.2).

6.) Iterate over the Query Range until the distance has reached a minimum and begins to grow larger. Retain the query identifier for the smallest distance.

7.) If the distance is within a maximum mapping window limit, set the Query Position into the peak.

8.) If a peak maps equally to two base calling positions, it is ambiguous. Issue a warning that the Peak cannot be mapped to a base call.

9.) Finally, all the unmapped peaks are deleted.

2.6 Stutter Processing

The purpose of the Stutter Processing module of step 414 in FIG. 4 is to eliminate signal noise which might give rise to false positive outcomes otherwise. Stutter is a well-known phenomenon associated with Sanger sequencing. It seems to frequently begin with homopolymorphic region and then can continue throughout the trace or come to an end. It can generally be easily recognized by manual inspection, but it has been difficult to detect and remove with a high degree of accuracy through automated processing.

Figure 22:
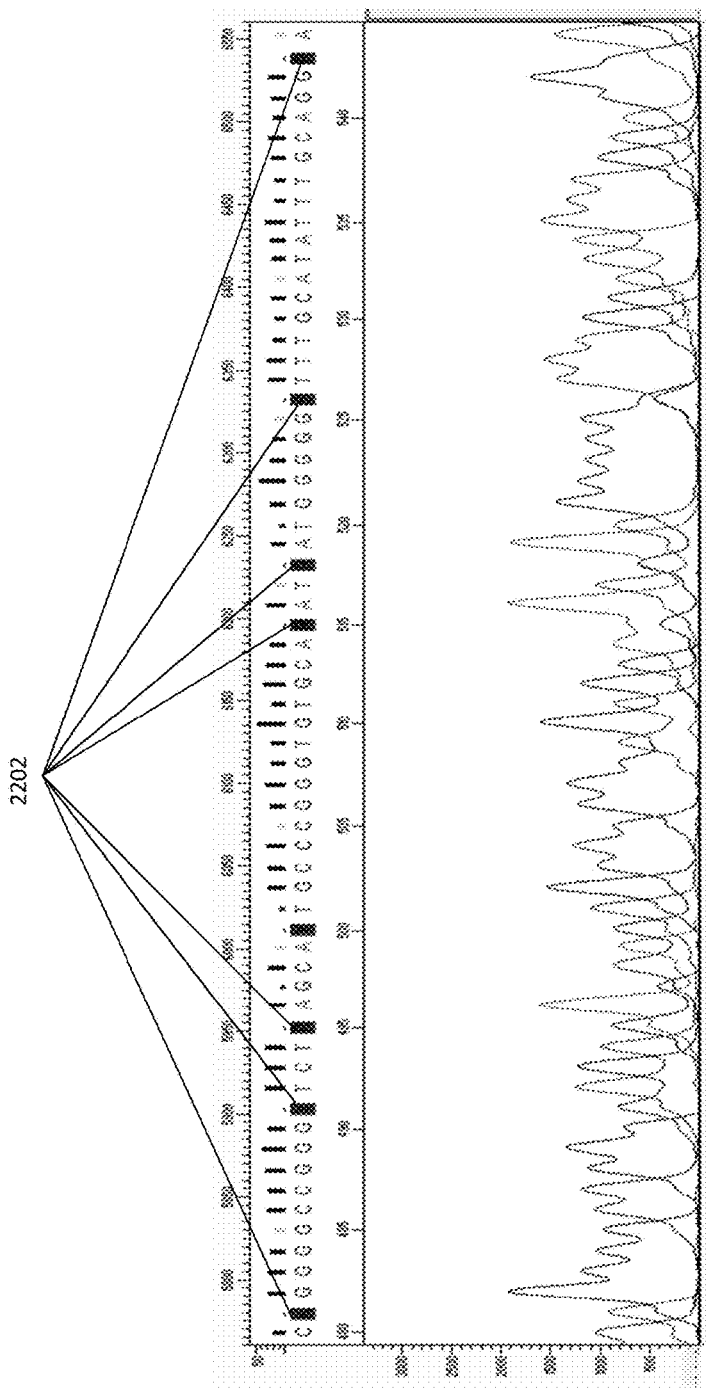
FIG. 22 illustrates an example of a stutter characteristic according to various embodiments described herein.

FIG. 22 provides a good example of stutter. Note the mixed base calls (2202.) Examination of the trace shows that these occur each time there is a legitimate tall peak preceded by a diminutive peak, the stutter peak, which falls beneath another legitimate peak.

Figure 23:
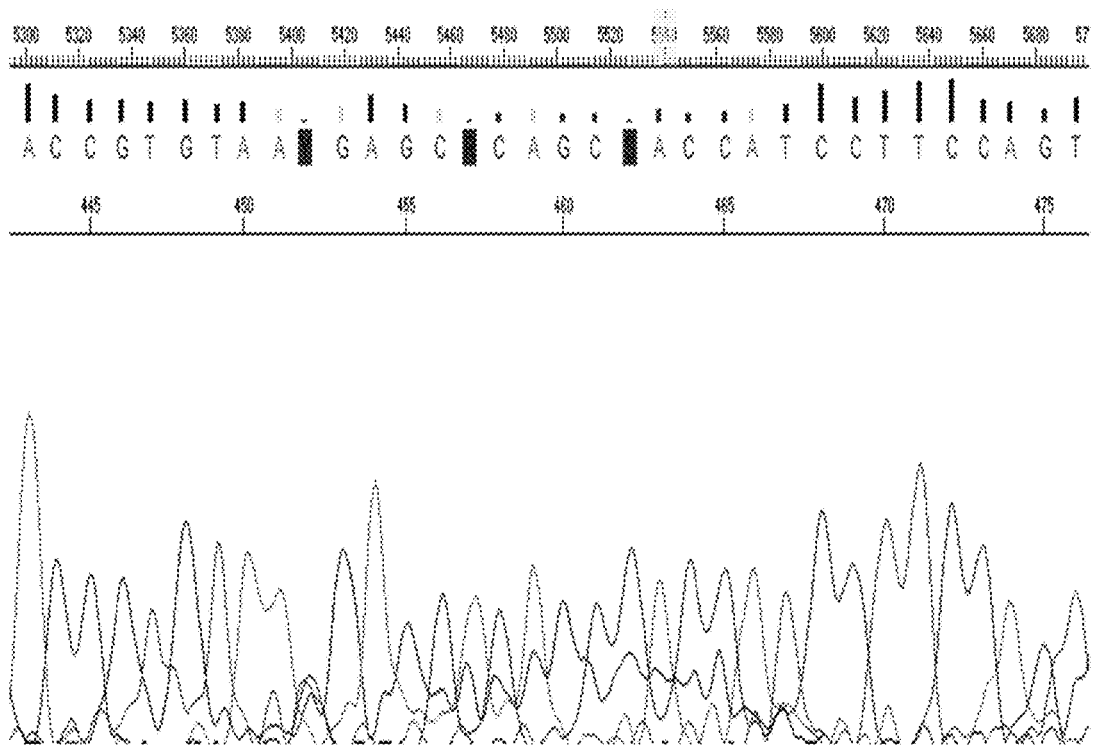
FIG. 23 illustrates an example of a characteristic which may be mistaken for stutter according to various embodiments described herein.
Figure 24A:
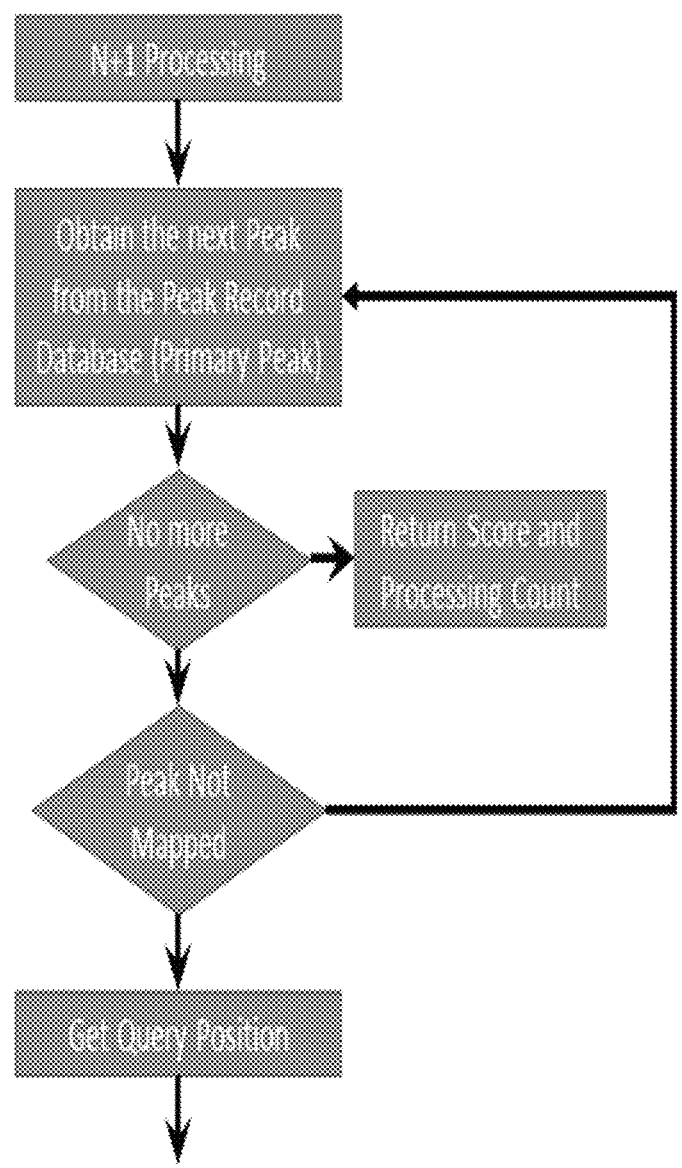
FIG. 24A-24E illustrates an example of stutter detection according to various embodiments described herein.
Figure 24B:
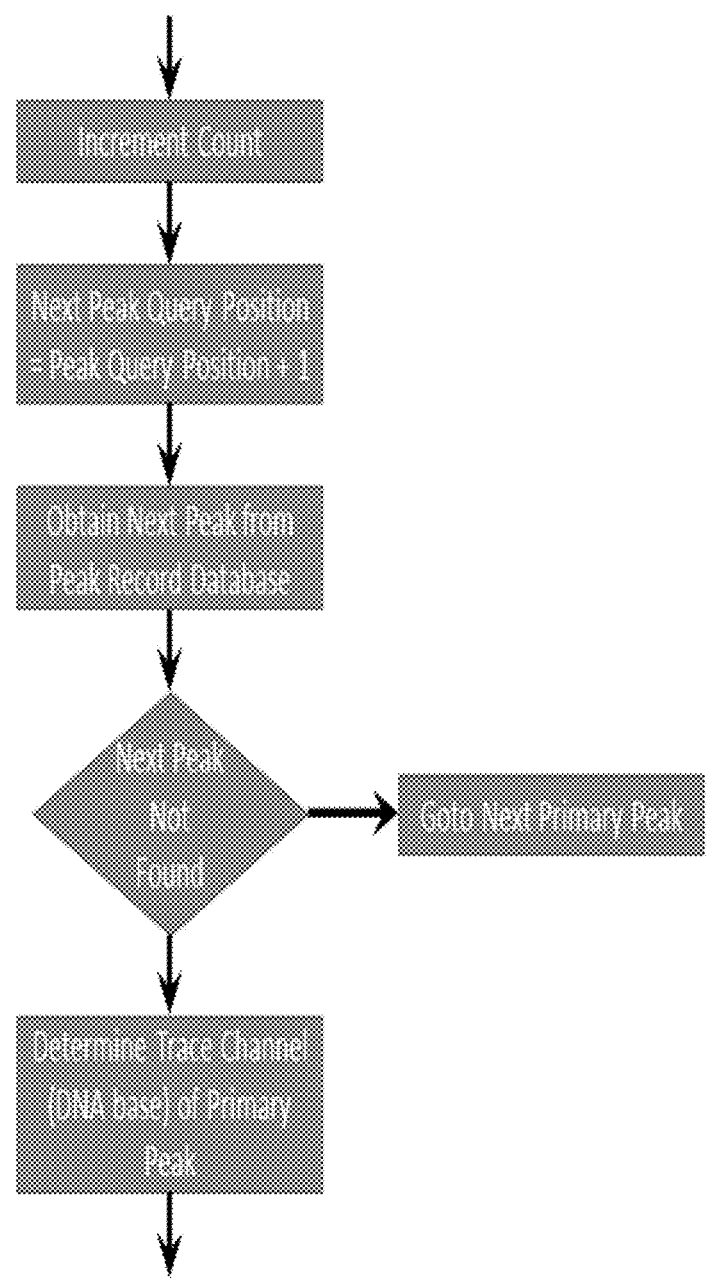
Figure 24C:
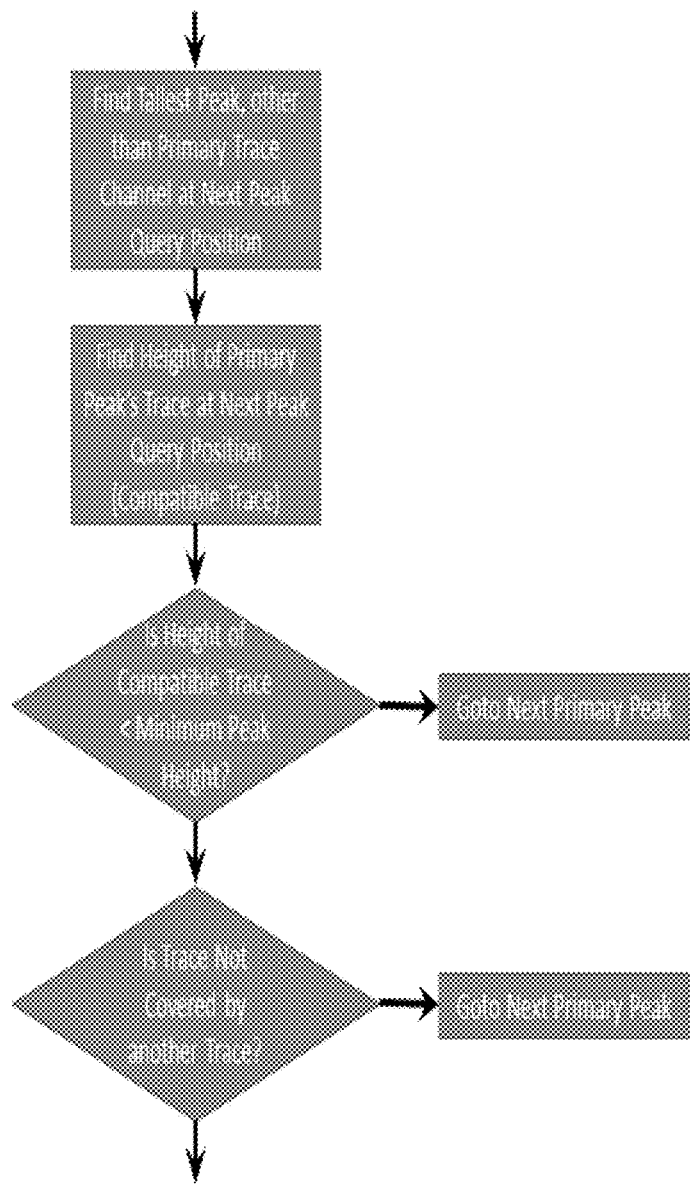
Figure 24D:
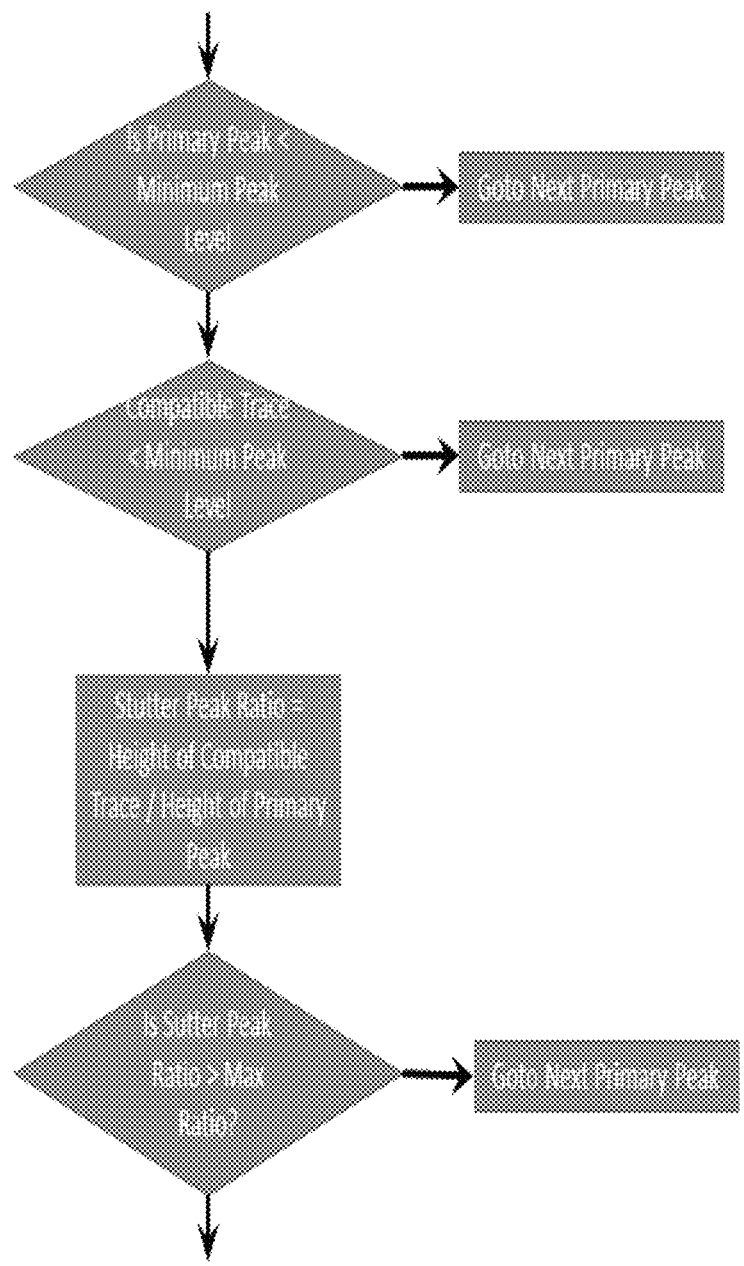
Figure 24E:
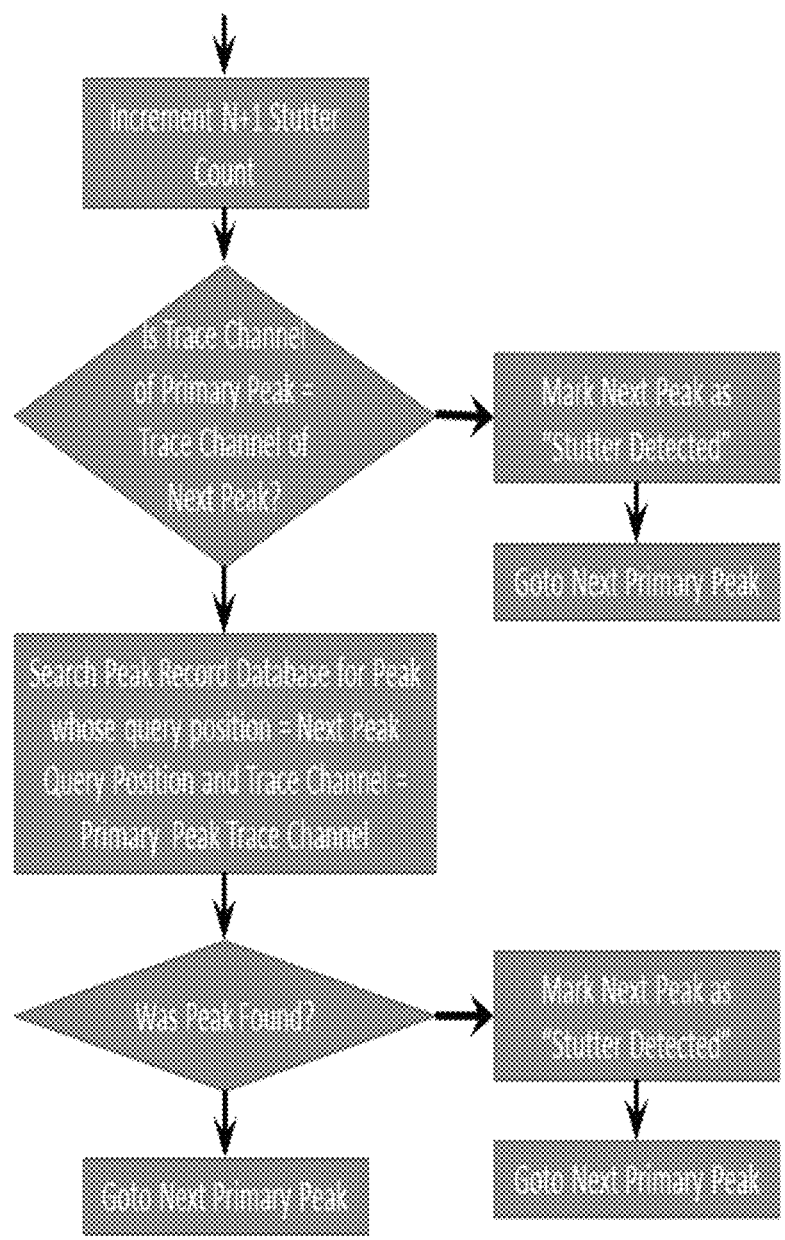
Figure 25A:
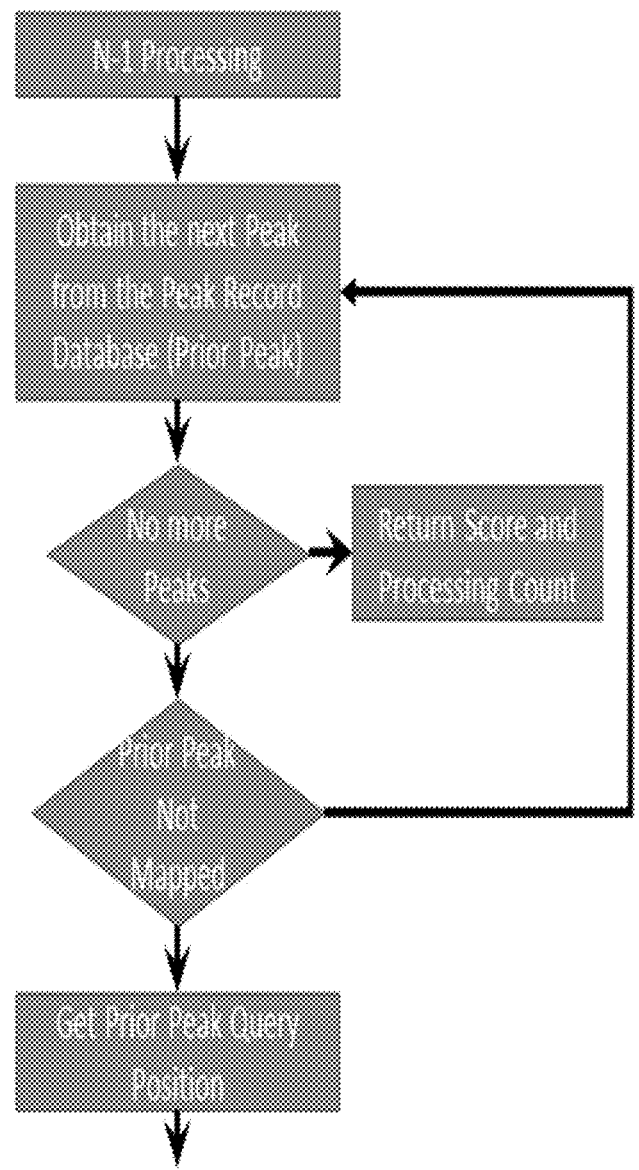
FIG. 25A-25E illustrates another example of stutter detection according to various embodiments described herein.
Figure 25B:
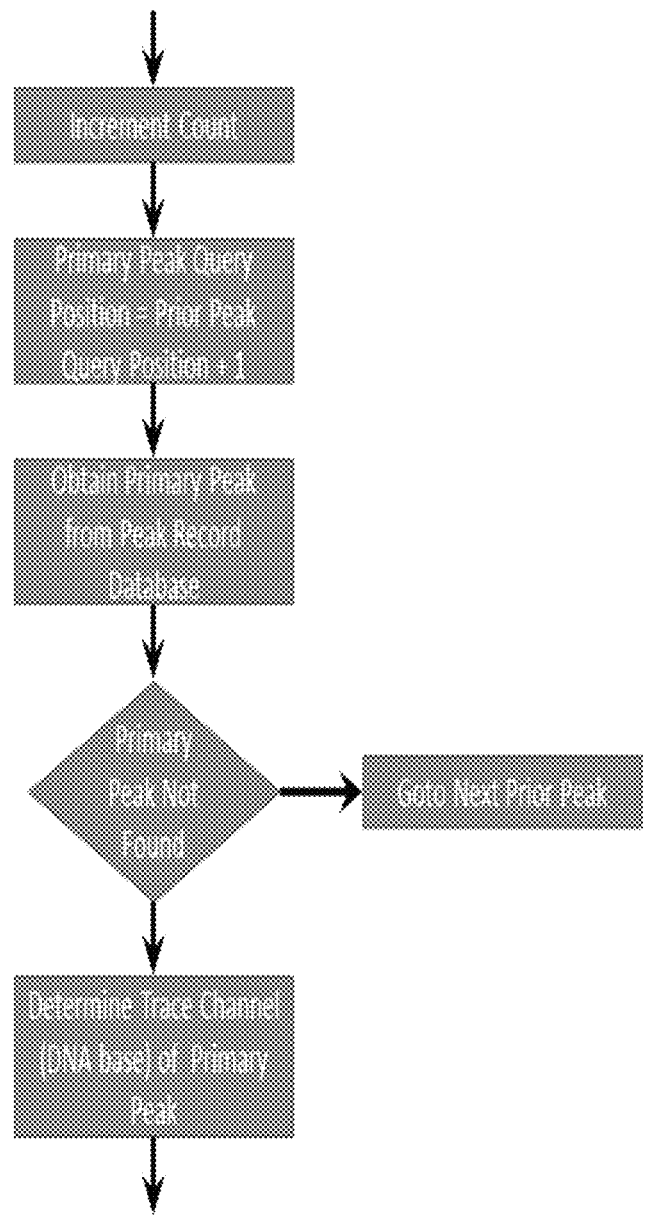
Figure 25C:
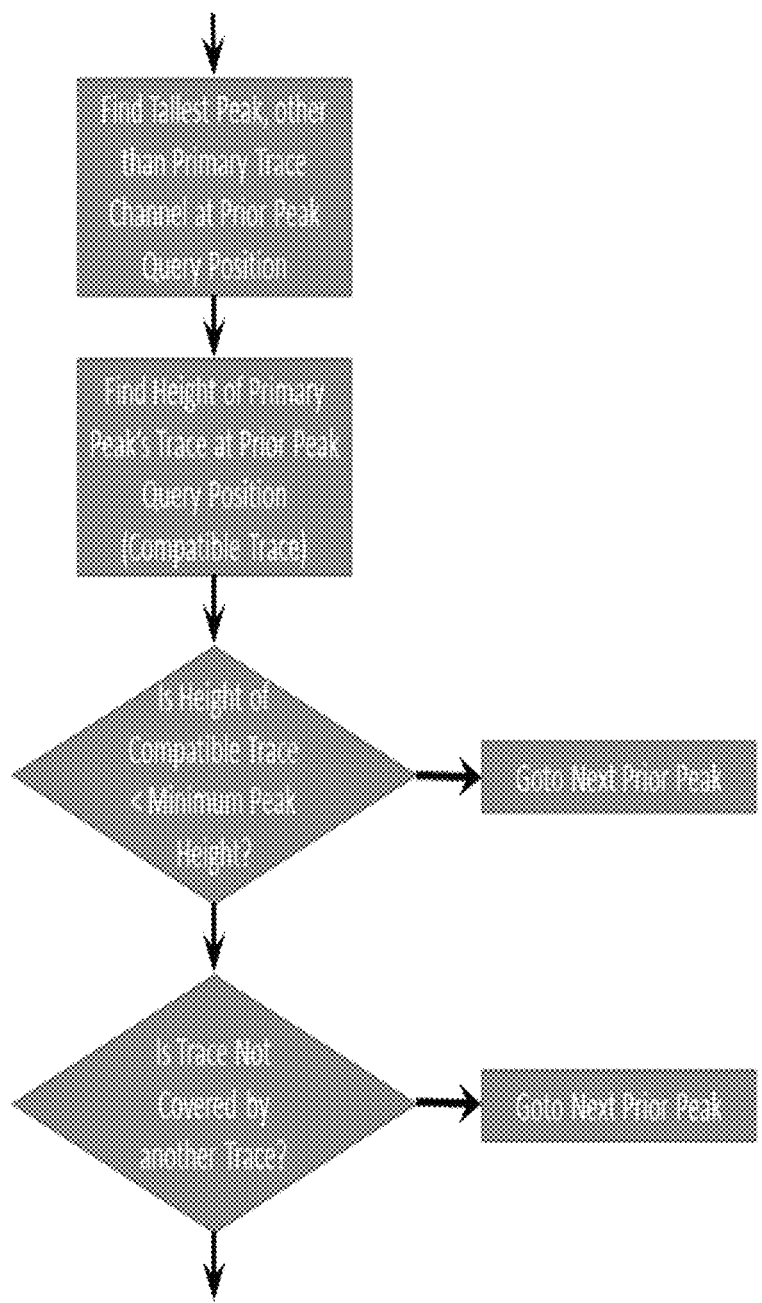
Figure 25D:
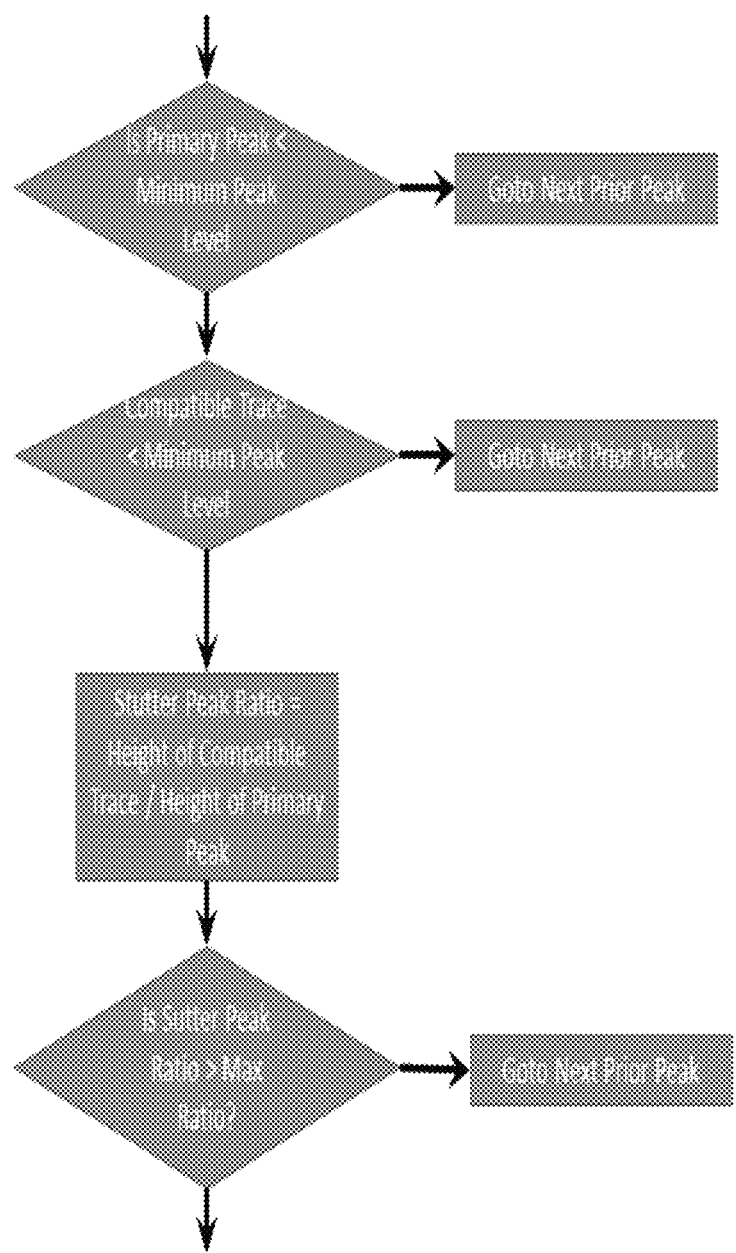
Figure 25E:
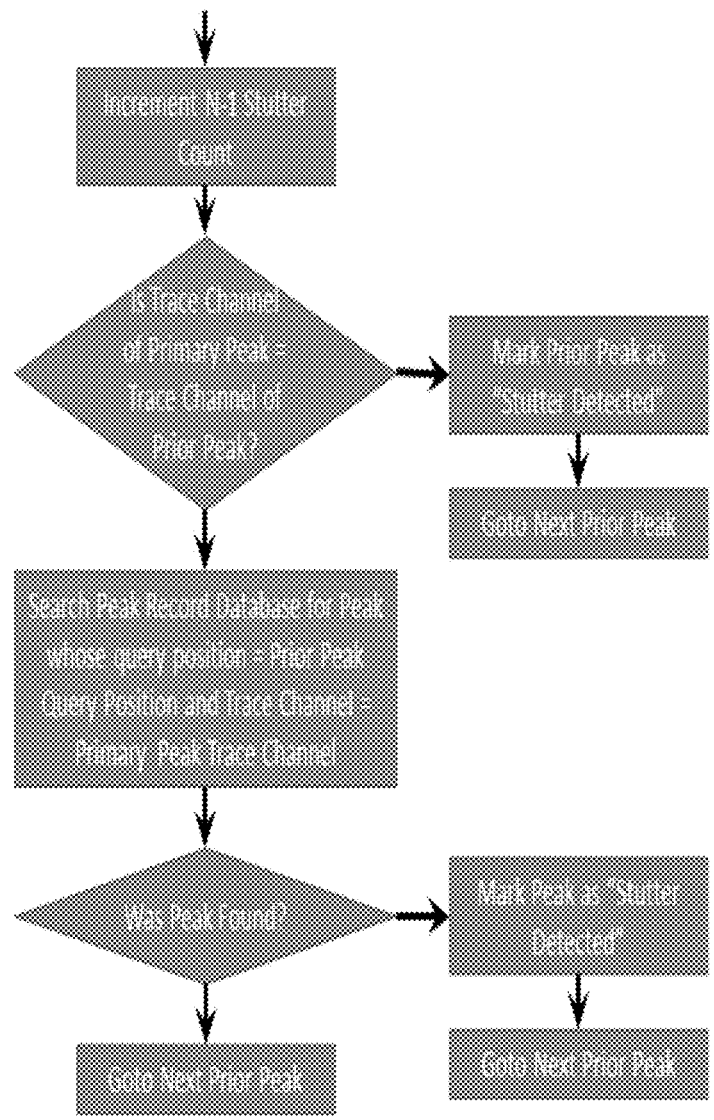

FIG. 23 shows an example of a trace which has many characteristics of stutter, but is not.

We are careful about eliminating stutter peaks because not every mixed base results from stutter and not every time a small peak follows a tall peak is that invalid. The approach, according to various embodiments, is to apply a set of rules to the trace region that generally characterize stutter to produce a stutter score, then if the score is high enough, the stutter module of the peak is removed.

We have developed a unique set of rules which we apply to trace regions around a mixed base variant to determine if stutter removal should be applied. These rules are:

1.) Stutter detection is only applied to traces which have a high mixed-base rate. This is because incidental mixed bases are almost never stutter, and traces with stutter phenomena typically have a marked increase in the mixed-base rate.
2.) Incidental observations of stutter are not absolute, however review of a trace region around the point of interest can discriminate stutter. This happens in part because the traces around a stutter region are frequently "busy" already and so sometimes detection can be confused. Also, the tuning of detection filters, to operate over a wide range and variation of traces sacrifices some determination.
3.) Stutter peaks are characterized by a taller peak followed by, or proceeded by a diminutive peak which is always below another peak. The diminutive peak is the stutter peak, and it should not enter into analysis.
4.) The stutter peak may proceed or follow the primary peak, and the pattern of leading or following will remain set throughout an entire stutter region, however determination of this in a short trace region is not possible due to phasing effects. However, determining stutter using a "both ways" stutter detection will resolve issues regarding directionality.
5.) The heights of the primary peaks and stutter peaks can be separated and used as a filter. Our analysis has revealed a range of heights between which stutter can be discriminated from simple noise, for example, and also from clear subsequent signals.
6.) The ratio of the primary and stutter peak can be further used to discriminate stutter from legitimate signals. To apply a sharp deadband on heights, we must also specify a ratio into which stutter peaks must fall. For example, two peaks which are nearly the same height cannot be stutter.
7.) Stutter peaks which are too low should be ignored. These will also be below the detection limit required to generate or support a call.
8.) For stutter detection, it is desirable for sensitivity to check trace height rather than require a peak detection. The stutter peaks may not be detected as peaks, but still can support a general detection of stutter.
9.) It is desirable to detect stutter in a trace region, even if it lends no specific identification of a stutter peak because the calls in a stutter region are less reliable than those in a clean region. We tag peaks differently if they are detected as a stutter peak or if they are in a region of stutter presence for use in scoring.

2.6.1 Stutter Processing
1.) Consider the ratio of the count of mixed-base occurrences called by KB Caller and the count of all the bases.
2.) If the ratio exceeds a threshold, subject the trace to stutter processing, otherwise do not process it for stutter.
3.) Sort the peaks based on the query position
4.) Calculate the stutter rate
5.) Compute a stutter score from the stutter rate
6.) Apply this stutter score to all the peaks in the Peak Record Database
7.) If the peak is not a stutter peak, set a flag to mark it as Associated with Stutter.

2.6.2 Stutter Rate Calculation
1.) Compute the NP1 stutter counts and also the number of peaks processed.
2.) Compute the NM1 stutter counts and also the number of peaks processed.
3.) Convert these counts into an NP1 and a NM1 rate.
4.) Compute a summarized stutter rate as the sum of both rates, limited to 1.0

2.6.3 Compute NP1 Stutter
FIGS. 24A-24E are described as follows:
1.) Process every peak in the Peak Record Database as the Primary Peak in step 2402.
2.) If the Primary Peak's Query Position has not been mapped, proceed to the next Primary Peak.
3.) Obtain the Primary Peak's Query Position.
4.) Increment the number of NP1 Peaks Processed.
5.) Increment the Primary Peak's Query Position to produce a Next Peak Query Position.
6.) Access the Peak Record Database to obtain the Next Peak using the Next Peak Query Position. If the Next Peak cannot be obtained, proceed to the next Primary Peak.
7.) Determine the trace channel (DNA base) of the Primary Peak.
8.) Find the tallest trace, other than the Primary Peak's trace channel, at the Next Peak Query Position.
9.) Find the height of the Primary Peak's trace channel at the Next Peak Query Position. This is the Compatible Trace.
10.) If the Compatible Trace's height is below the Minimum Trace Height value, then it cannot be considered for a stutter peak and proceed to the next Primary Peak.
11.) If the Compatible Trace is not below another trace, then it cannot be considered as a stutter peak and proceed to the next Primary Peak.
12.) If the Primary Peak's height is below a minimum level, then it cannot be considered as a stutter peak and proceed to the next Primary Peak.
13.) If the Compatible Trace's height is below a Minimum Trace Height Level then it cannot be considered as a stutter peak and proceed to the next Primary Peak.
14.) Determine the ratio of the height of the Compatible Trace to the Primary Peak. If the ratio is greater than a Maximum Stutter Peak Ratio, then is cannot be considered as a stutter peak and proceed to the next Primary Peak.
15.) The findings are consistent with stutter detection. Increment the NP1 Stutter Count.
16.) If the Next Peak has the same trace channel as the Primary Peak Trace Channel, then mark it as "Stutter Detected", otherwise search through the Peak Record Database for a peak with the same trace channel as the Primary Peak Trace Channel and with a Query Position of the Next Query Position. If found, mark that peak as "Stutter Detected."
17.) Proceed to the next Primary Peak.

2.6.4 Compute NM1 Stutter
FIGS. 25A-D are described as follows:
1.) Process every peak in the Peak Record Database as the Prior Peak.

2.) If the Prior Peak's Query Position has not been mapped, proceed to the next Prior Peak.
3.) Obtain the Prior Peak's Query Position.
4.) Increment the number of NM1 Peaks Processed.
5.) Increment the Prior Peak's Query Position to produce a Primary Peak Query Position.
6.) Access the Peak Record Database to obtain the Primary Peak using the Primary Peak Query Position. If the Primary Peak cannot be obtained, proceed to the next Prior Peak.
7.) Determine the trace channel (DNA base) of the Primary Peak.
8.) Find the tallest trace, other than the Primary Peak's trace channel, at the Prior Peak Query Position.
9.) Find the height of the Primary Peak's trace channel at the Prior Peak Query Position. This is the Compatible Trace.
10.) If the Compatible Trace's height is below the Minimum Trace Height value, then it cannot be considered for a stutter peak and proceed to the next Prior Peak.
11.) If the Compatible Trace is not below another trace, then it cannot be considered as a stutter peak and proceed to the next Prior Peak.
12.) If the Prior Peak's height is below a minimum level, then it cannot be considered as a stutter peak and proceed to the next Prior Peak.
13.) If the Compatible Trace's height is below a Minimum Trace Height Level then it cannot be considered as a stutter peak and proceed to the next Prior Peak.
14.) Determine the ratio of the height of the Compatible Trace to the Primary Peak. If the ratio is greater than a Maximum Stutter Peak Ratio, then is cannot be considered as a stutter peak and proceed to the next Prior Peak.
15.) The findings are consistent with stutter detection. Increment the NM1 Stutter Count.
16.) If the Prior Peak has the same trace channel as the Primary Peak Trace Channel, then mark it as "Stutter Detected", otherwise search through the Peak Record Database for a peak with the same trace channel as the Primary Peak Trace Channel and with a Query Position of the Prior Query Position. If found, mark that peak as "Stutter Detected."
17.) Proceed to the next Prior Peak.

2.7 Merge Peaks

The purpose of the Merge Peaks function in step 416 of FIG. 4 is to combine independent pure-base signals into mixed-base detections. Mixed bases can occur when we have detected two peaks that map onto the same query position.

2.7.1 Identify Merge Candidates
1.) Sort the peaks in ascending query position.
2.) Traverse the peaks from first to last query position considering each in turn.
3.) Obtain the peak's query position. Skip any unmapped peaks.
4.) If this is the first peak, then add the peak to the merge candidates list.
5.) Otherwise, if this peak's query position matches the last peak's query position then added to the merge candidates list and process the merge candidate list as described in section 2.7.1 and empty it.
6.) Add the considered peak into the merge candidate list.
7.) Continue until all the peaks have been considered and processed.

2.7.2 Process Merge Candidates

The goal of this module is to create a final list of base calls for subsequent interpretation and for variant scoring. Specifically, this module merges multiple peaks mapping to the same query position into a single peak. It attempts to make the best choices with a bias to reproduce the base call produced by KB Caller. The reason for this is not to slovenly reproduce KB results, but to rather assemble the same trace configuration that KB used in order to produce the variant score. In cases where it is not possible to reproduce the KB configuration of bases, the best peaks are selected, the most highly modulated, as the base candidate. The following steps describe this process.

1.) Obtain the query position for the items in the merge candidates list.
2.) Obtain the base call produced by KB Caller for that query position.
3.) If the KB Caller called base is a pure base, then
   a. Select the candidate from the merge candidate list which matches the KB called base and add it to the merged bases list.
   b. If no matching base can be found, select the candidate which has the greatest modulation from the merged peaks list.
4.) If the KB Caller called a mixed base
   a. Hunt through the merge candidates list in an attempt to find bases which are compatible to the KB called base. Compatible means each is a module of the mixed base.
   b. If we found two compatible mixed bases, then If the first peak has a greater modulation than the second peak, add the second peak onto the first peak as a secondary peak. Otherwise, add the first peak onto the second peak as a secondary peak. In either case, add them to the merged bases list.
   c. If we only found a single compatible base, then add it to the merged base list.
   d. If neither of these cases is true, then find the peak with the greatest modulation. Add, if available, the peak with the next greatest modulation to it as a secondary peak. Add the peak to the merged peaks list.

Mixed-Base Variant Scoring

It is difficult to obtain his sensitivity and high rejection base on a basic morphological analysis of an electropherogram trace with a diverse set of traces and with the wide variety of phenomena that may be observed. Specifically, it is hard to discriminate between "good" peaks and "bad" peaks because of the lack of absolute standards of such, and because the factors involved are myriad. Any such standard established for pass and fail are subject to inaccuracies and cause either too may rejections (false negatives) or too few rejections (false positives.) One approach is to utilize a training set to develop classifiers for applying to traces, but the development of these classifiers is non-trivial and the ability to validate coverage is a daunting task. It is complicated due to nuances, which are difficult to automate.

The Solution

Multiple approaches are combined to solve the problem.
1.) Trace based metrics. A standard set of trace based metrics are collected during processing. These metrics are basic such as peak overlap, peak height, and modulation. These peak metrics provide a common perspective into the morphology of the trace and form the basis of our scoring.
2.) Dual-Hypothesis. We consider the hypothesis that the KB Caller has produced a correct interpretation of the electropherogram and that its base call is correct, and we also consider the hypothesis that instead the correct call is a match to the reference. The dual hypothesis approach provides a differential signal which enables us to discriminate between apparently good calls, apparently bad calls, and indeterminable calls. That is, if the hypothesis for a match with the KB Caller is strong and the match with the reference is poor, then the call is good. If the match with the reference is good and the match with the KB caller is poor, then the call is likely bad. If both the KB Caller hypothesis and the Reference Hypothesis are poor, then the call confidence is poor.

3.) Other trace based metrics. In addition to the basic trace metrics, we include recognition of specific defects which impact the reliability of variant calling, such as end effects, stutter, and peak spacing. These point out common characteristics that can be scored.

4.) Utilization of Pairing. We use pairing information, which available to strengthen or refute variant calls. A pair is a forward and reverse read taken from a single biological specimen. In principle, it should lend identical base calls, however due to end effects and primer effects, this is seldom the case. Still, when the complementary read reinforces the call, the confidence is bolstered!

Variant Scoring Implementation
Calculation of Trace Based Metrics

The following trace based metrics comprise the Trace Based Metrics as described below:

Squares Score

The purpose of the Squares Score is to compute metrics for the degree to which the KB hypothesis is validated or refuted, and the degree to which the Reference hypothesis is validated or refuted based on overlaps with the scoring peak. The Square Scores is a score of the expected pure base or expected mixed-base. The Square Score validates the detection of the expected base(s). Next, the Square Score computes a score based on the overlap for both the KB hypothesis and also for the Reference hypothesis. The computation of overlap has been previously described in the Trace Analysis section.

Error! Reference source not found. 26 illustrates the automation of the computation of the Square Score for a pure base assertion. The pure base assertion may arise from computation of the KB Caller hypothesis or from the Reference Hypothesis. As shown in Error! Reference source not found. 27, overlap will lower the score once a (configurable) overlap threshold has been reached. In the first case, there is limited background noise but it is below the overlap threshold and the peak Square Score would be high. In the second case, the intersection of a single peak is far above the overlap threshold and so the Square Score would be low. This would occur in the case of a mixed-base that has been incorrectly identified as a pure base. The third example show excessive background noise that challenges the pure base call. Because the overlap due to the other traces is somewhat above overlap threshold, the Square Score would be lowered.

Figure 27:
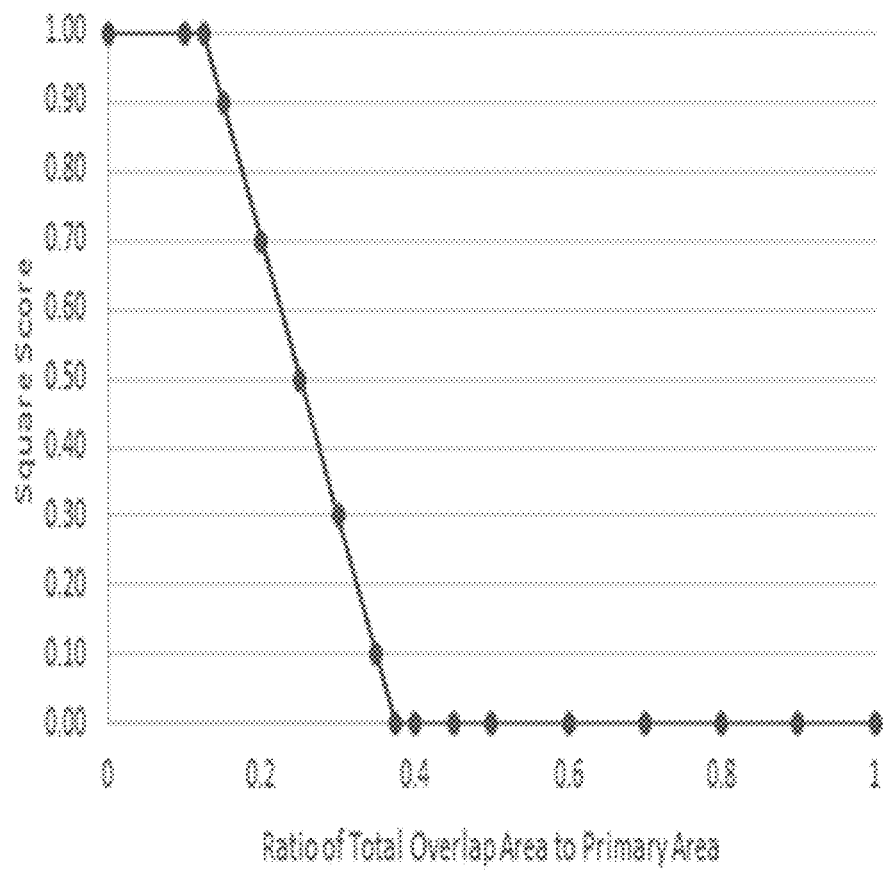
FIG. 27 illustrates a square score computation according to various embodiments described herein.

As shown in FIG. 27, we have used a linear approach to score generation based on peak overlap. The breakpoints are configurable and tunable to achieve the highest performance.

Figure 29:
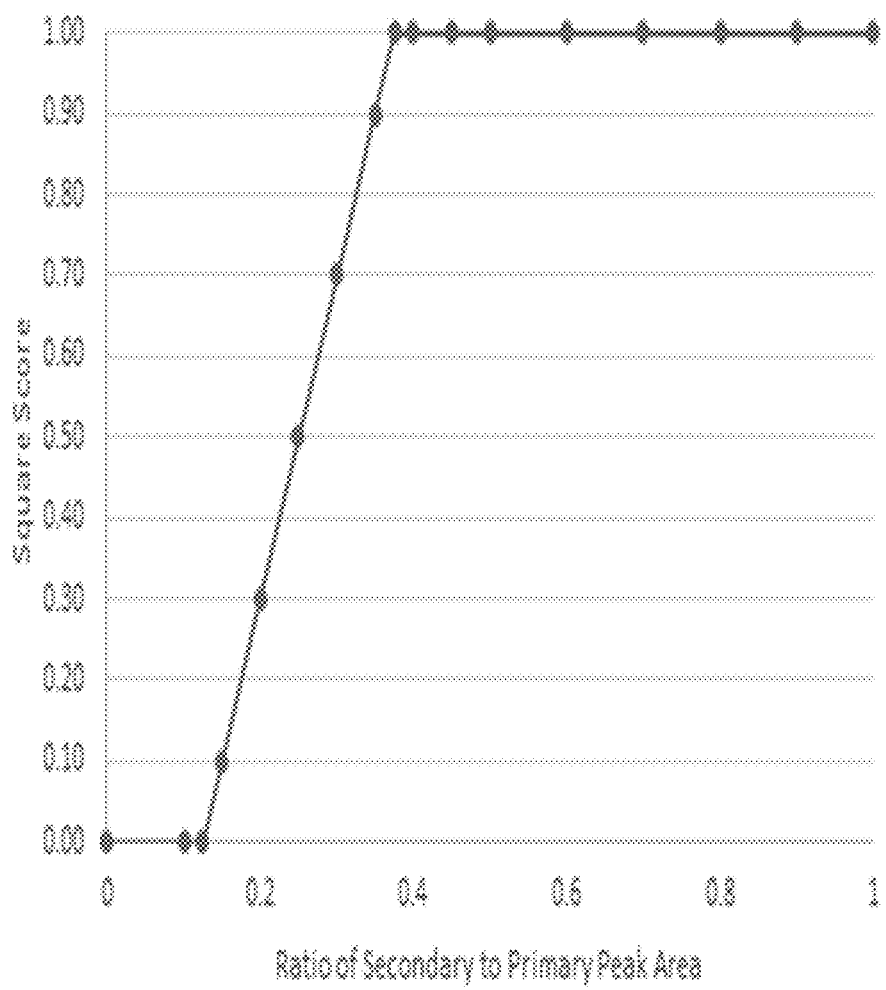
FIG. 29 illustrates a mixed base square score computation according to various embodiments described herein.

FIG. 28 illustrates the automation of the computation of the Square Score for a mixed-base assertion. The mixed-base assertion could arise from computation of the KB Caller hypothesis but not from the Reference Hypothesis as the reference sequence is pure-base. As shown in FIG. 29, appropriate overlap is required for a good Square Score.

For mixed bases, the overlap is computed for the expected secondary peak on the primary peak, and also for the overlap of the other peaks on the secondary peak. If the overlap of the other peaks on the secondary peak exceeds a threshold, then we determine an interference score which will lower the Square Score outcome for the mixed-base assertion.

In the first case, there is clean overlap of the expected secondary peak on the primary peak. The Square Score would be high. In the second case, the intersection of a single peak is weak due to low amplitude and an offset in displacement. Because the overlap is low, the Square Score would also be low. The third example shows excessive background noise that challenges the pure base call. Because the overlap due to the other traces is somewhat above overlap threshold, the Square Score would be lowered.

As shown in FIG. 29, we have used a linear approach to Squares Score generation based on peak overlap.

Figure 30:
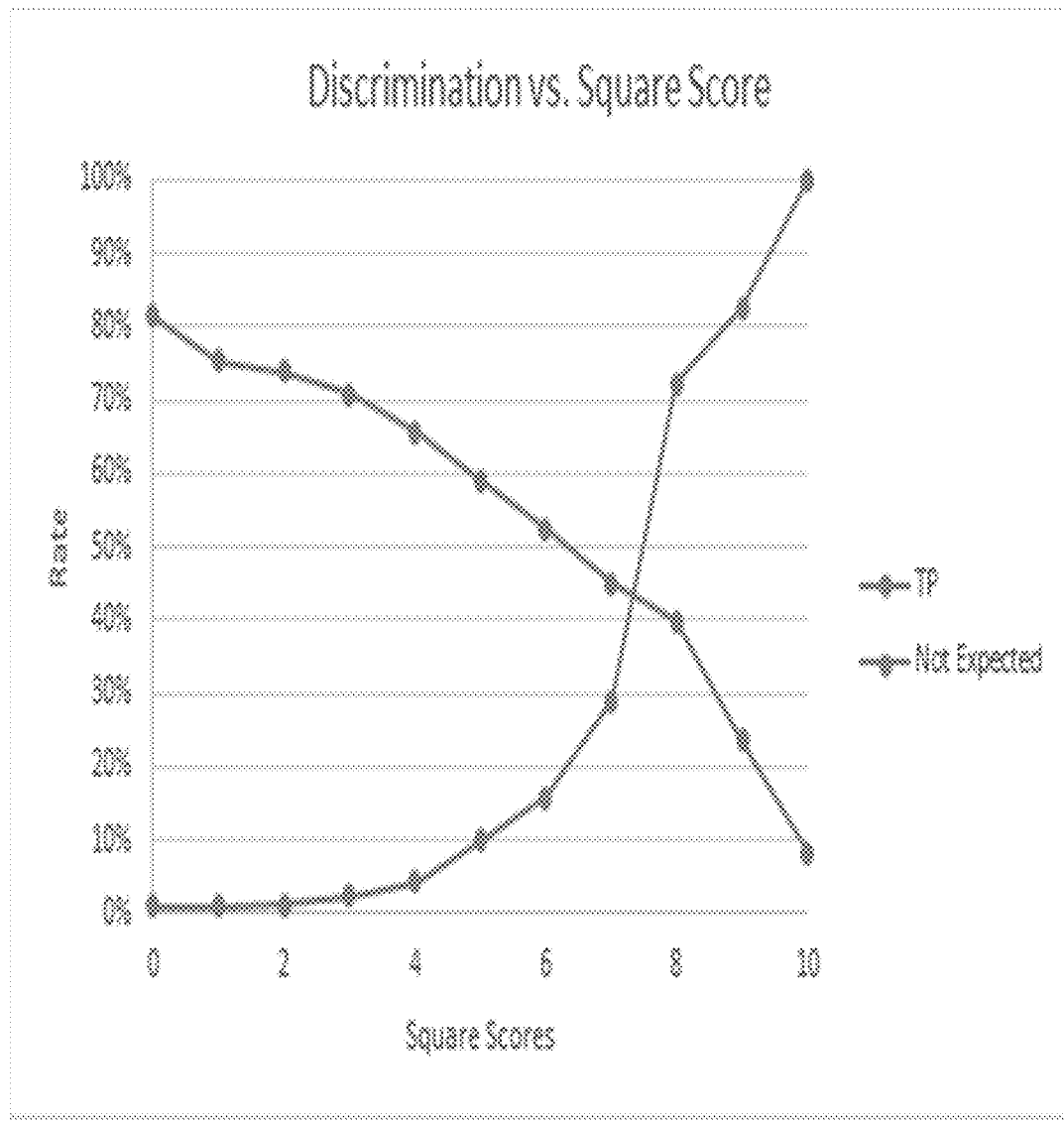
FIG. 30 illustrates an example of a square scores discrimination according to various embodiments described herein.

FIG. 30 shows the discrimination derived from Squares Score to rank true positive and false positive outcomes. The graph is based on execution of a large set of expertly curated data and shows good performance, with a cross over at a score around 7.5.

Amplitude Score

Figure 31:
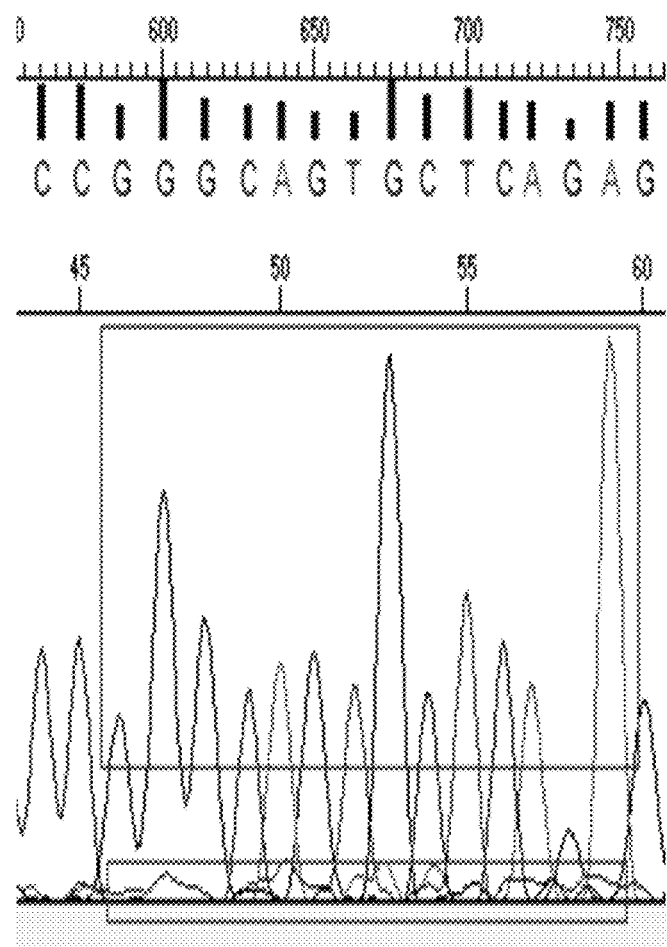
FIG. 31 illustrates an example of amplitude as a measure of confidence according to various embodiments described herein.
Figure 32:
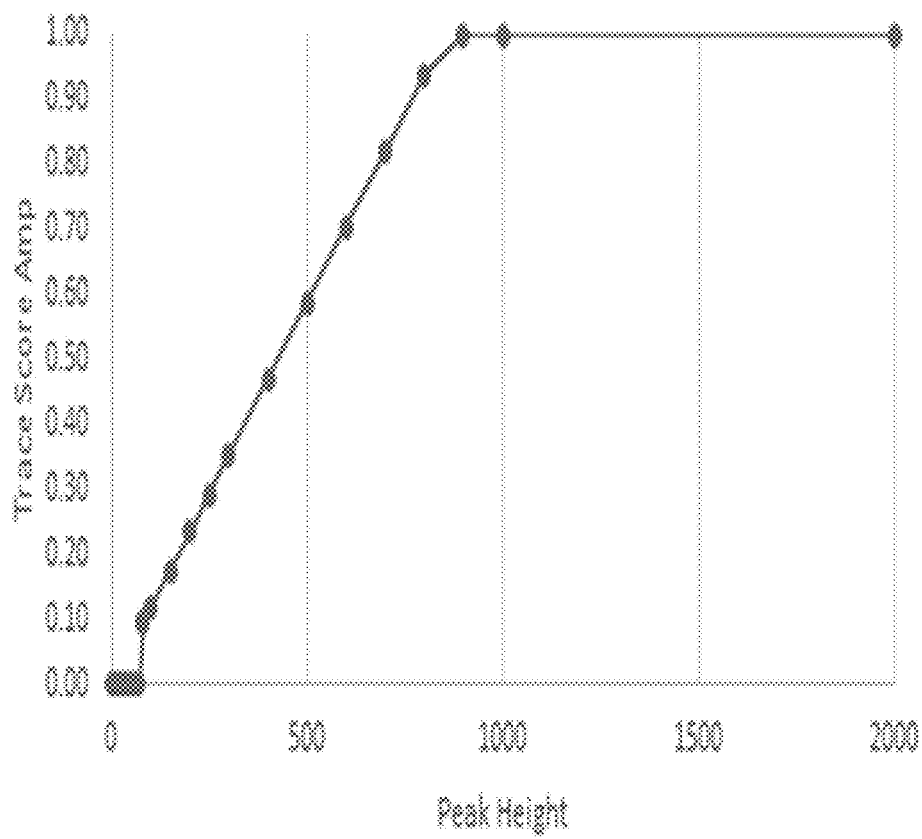
FIG. 32 illustrates an example of amplitude score computation according to various embodiments described herein.

The Amplitude Score computes a score for the KB hypothesis and the Reference hypothesis based on the amplitude of the scoring peak. As illustrated in FIG. 31, in the upper red box, the height of the peak plays little role in discriminating good and bad peaks. All of these peaks are of the same quality. In the lower box, these peaks are noise and cannot confidently contribute to a variant call. The Amplitude Score is consequently a qualifier of confidence rather and a continuous discriminator of good/bad variant confidence. A further note is that the Trace Analysis module has removed low-level peaks prior to scoring.

The amplitude score is based on parameters which are set during tuning. The score is computed as follows:

1.) For pure bases, the detection of the asserted pure-base peak is validated. If the peak is not detected, a score of zero is returned for both the KB hypothesis and for the reference hypothesis. For mixed-bases the detection of both pure-base modules is validated. If the peaks are not detected, a score of zero is returned for both the KB hypothesis and for the reference hypothesis.

2.) A mixed-base height ratio is compute if a secondary peak is identified. In this case, the ratio of the heights of the secondary to primary peak is computed. This height is converted to a score based on a linear mapping similar to that described in the Squares Score computation above.

3.) For pure bases, if the height of the primary peak falls below a minimum height threshold the Amplitude Score for the KB Caller and the reference hypothesis will both be set to zero. Otherwise the score will be determined by a linear mapping similar to that described for the Squares Score computation above. The score is reduced by the mixed base ratio computed in step 2.

4.) For mixed bases, the score for both modules is computed as described in step 3. Each score is contingent on the mixed-base score computed in step 2. The Amplitude Score is the lessor of the two scores.

Error! Reference source not found. 32 provides an illustration (actual thresholds and slopes may vary) for amplitude score computation.

Figure 33:
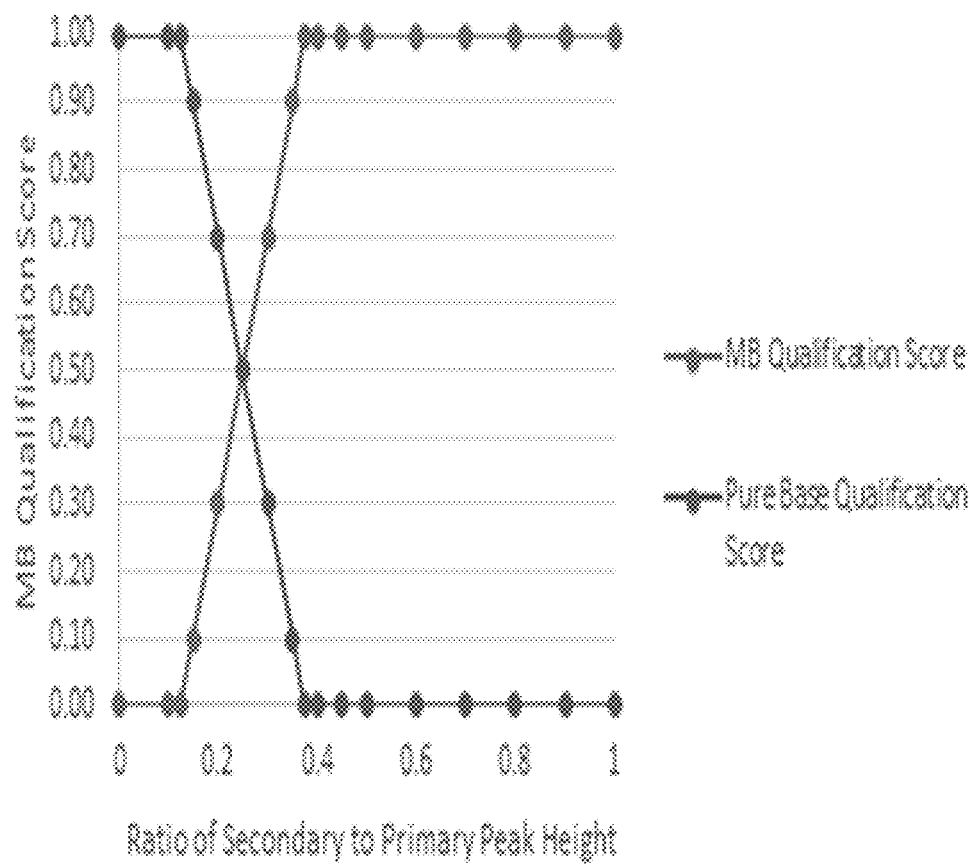
FIG. 33 illustrates an example of mixed-base ratio scoring according to various embodiments described herein.

FIG. 33 illustrates the computation of the mixed-base ratio scoring (thresholds and slopes may vary.) The score is designed to provide hard limits to rewards and benefits below and above certain thresholds, and to provide a linear range of reward/benefit in a short region between.

Figure 34:
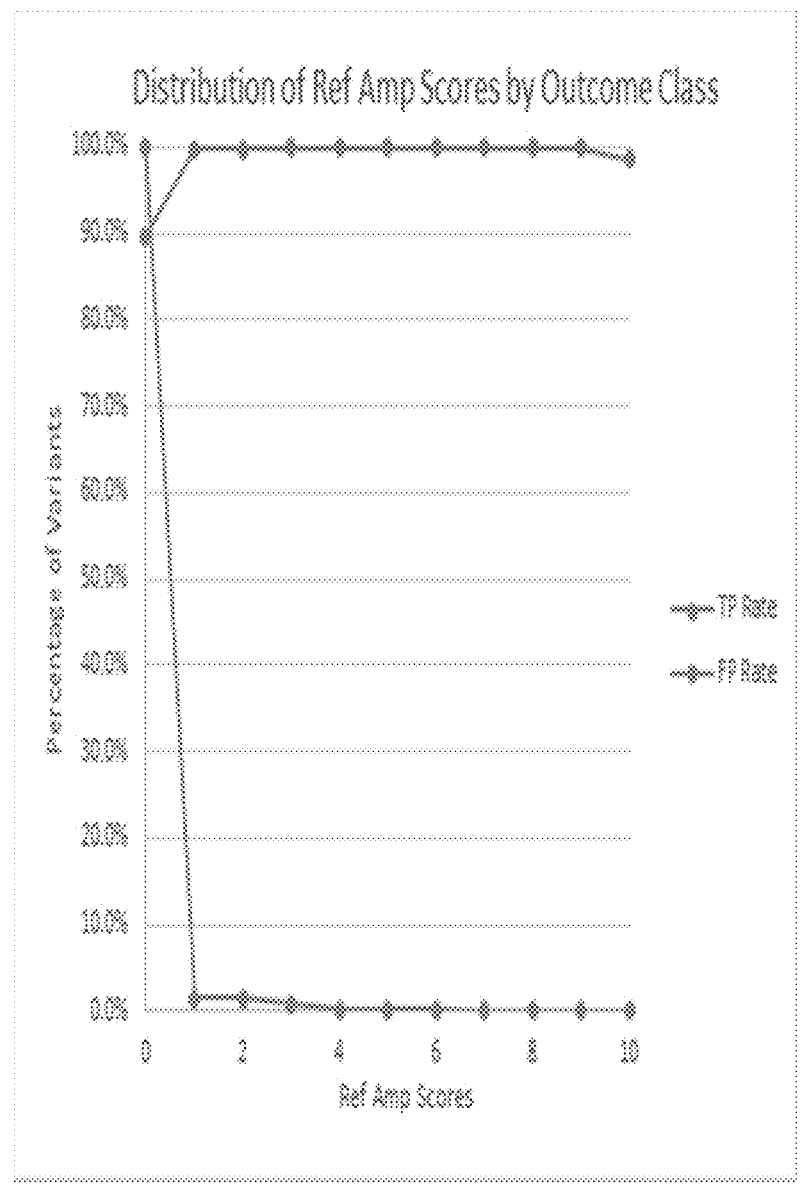
FIG. 34 illustrates an example of amplitude score performance according to various embodiments described herein.

FIG. 34 shows the performance of the amplitude score in discriminating true positive and false positive outcomes. As expected, the Amplitude score has little impact on most of the points, as the outcomes are not predicted by height. Discrimination of a small number of points is shown between amplitude scores of 0 and 1.

Modulation Score

The purpose of the Modulation Score is to compute metrics for the degree to which the KB hypothesis is validated or refuted, and the degree to which the Reference hypothesis is validated or refuted based on overlaps with the scoring peak. The Modulation Score is provided for the expected pure base or expected mixed-base. The Modulation Score algorithm validates the detection of the expected base(s). Next, the Modulation Score algorithm computes a Modulation Score based on the degree of modulation for both the KB hypothesis and also for the Reference hypothesis. The computation of modulation has been previously described in the Trace Analysis section.

FIG. 26 illustrates the mechanization of the computation of the Square Score for a pure base assertion. The pure base assertion could arise from computation of the KB Caller hypothesis or from the Reference Hypothesis. As shown in FIG. 27, overlap will lower the score once a (configurable) overlap threshold has been reached. In the first case, there is limited background noise but it is below the overlap threshold and the peak Square Score would be high. In the second case, the intersection of a single peak is far above the overlap threshold and so the Square Score would be low. This would occur in the case of a mixed-base that has been incorrectly identified as a pure base. The third example show excessive background noise that challenges the pure base call. Because the overlap due to the other traces is somewhat above overlap threshold, the Square Score would be lowered.

Figure 35:
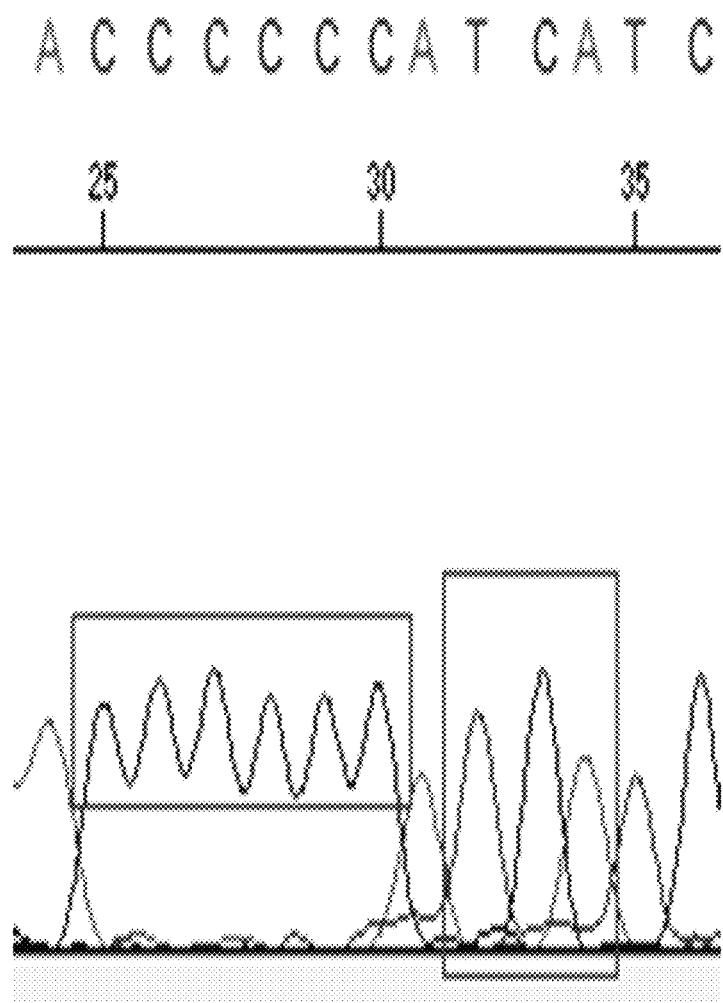
FIG. 35 illustrates an example of modulation as compared to amplitude according to various embodiments described herein.
Figure 36:
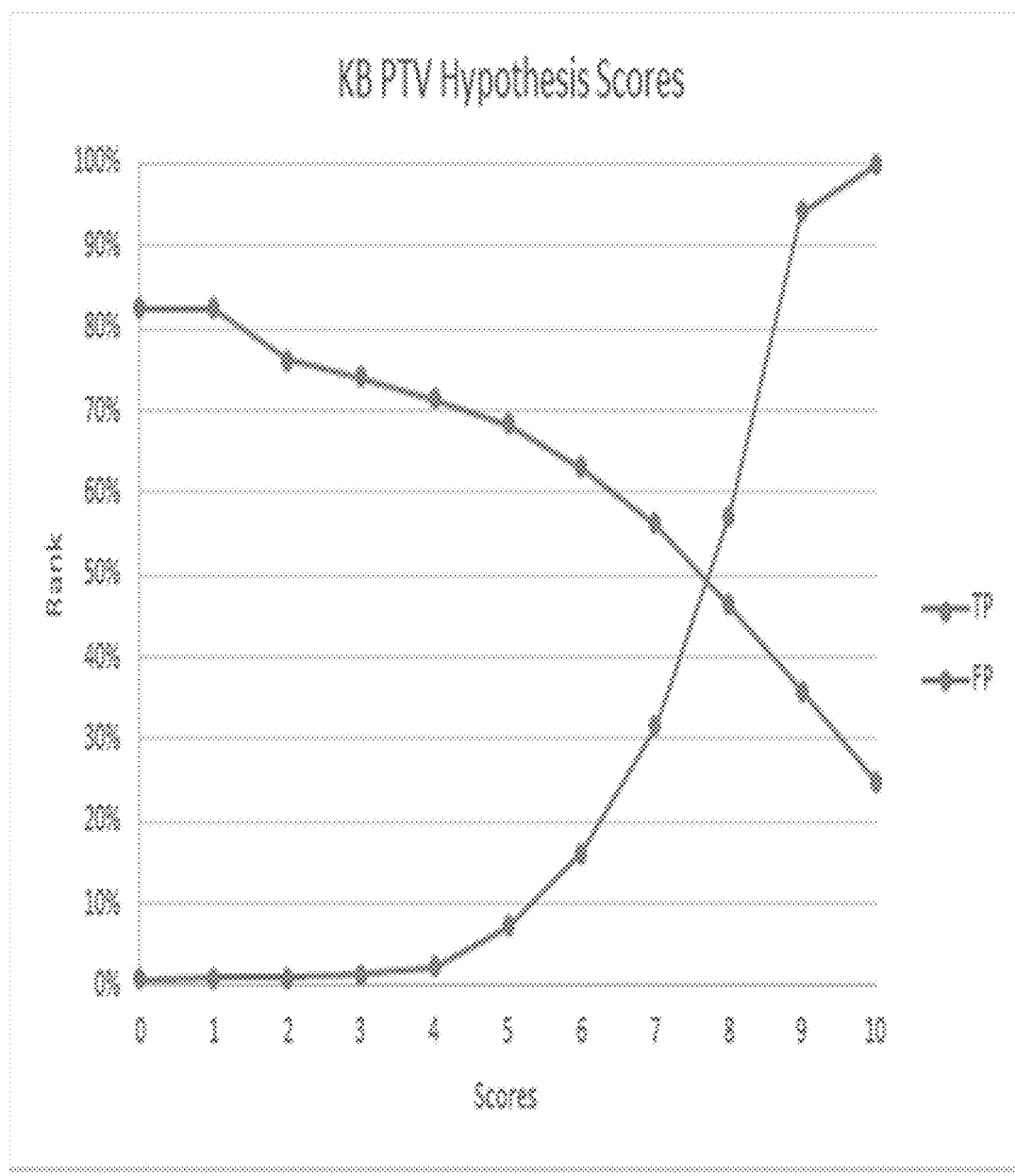
FIG. 36 illustrates an example of performance of modulation score according to various embodiments described herein.
Figure 37:
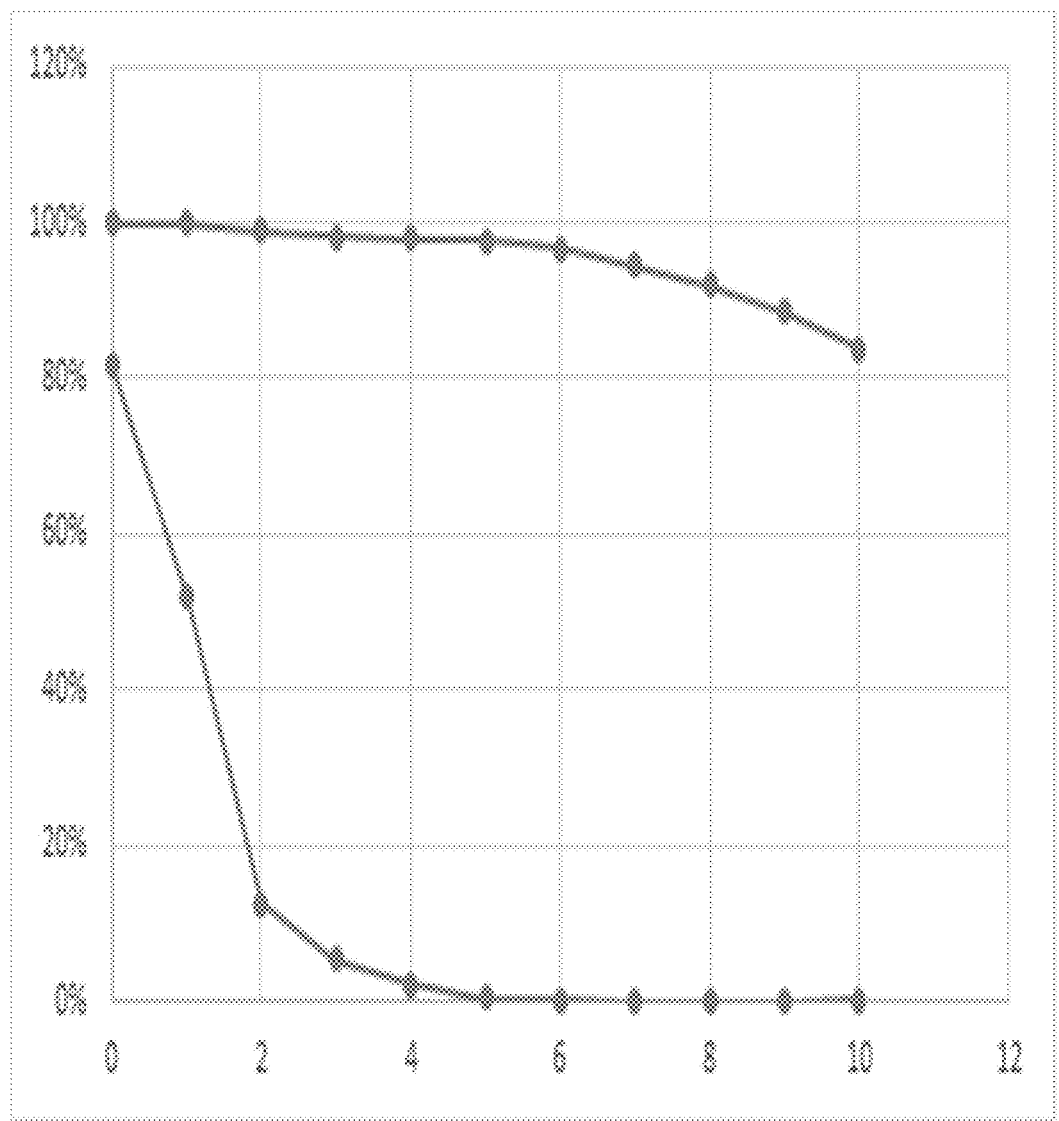
FIG. 37 illustrates an example of variant scores according to various embodiments described herein.

FIG. 35 shows the difference between modulation and amplitude and the degree to which signals can be reliably detected at high amplitudes and lower modulation versus lower amplitudes, which require higher modulation. In this figure, all the signals can be reliably captured and should not have any differential in reward/benefit.

The Modulation Score is based on parameters which are set during tuning. The score is computed as follows:

1.) For pure bases, the detection of the asserted pure-base peak is validated. If the peak is not detected, a score of zero is returned for both the KB hypothesis and for the reference hypothesis. For mixed-bases the detection of both pure-base modules is validated. If the peaks are not detected, a score of zero is returned for both the KB hypothesis and for the reference hypothesis.
2.) A mixed-base height ratio is compute if a secondary peak is identified as previously describe in the Amplitude Score computation.
3.) For pure bases, if the modulation of the primary peak falls below a minimum threshold the Modulation Score for the KB Caller and the reference hypothesis will both be set to zero. Otherwise the Modulation Score will be determined by a linear mapping similar to that described for the Squares Score computation above. The score is reduced by the mixed base ratio computed in step 2.
4.) For mixed bases, the Modulation Score for both modules is computed as described in step 3. Each Modulation Score is contingent on the mixed-base score computed in step 2. The Modulation Score is the lessor of the two scores.

Error! Reference source not found. 36 shows the discrimination derived from the modulation score (PTV) to rank true positive and false positive outcomes. The graph is based on execution of a large set of expertly curated data and shows good performance, with a cross over at a score around 7.5.

Dual Hypothesis Score

The above metrics are combined into a single metric for both the KB Hypothesis and the Reference Hypothesis as described following:

Effective Squares Score=min(Square Score,1.0)
*Squares Score Factor

Effective Amplitude Score=min(Amplitude Score, 1.0)*Amplitude Score Factor

Effective Modulation Score=min(Modulation Score, 1.0)*Modulation Score Factor

For both the KB Hypothesis score and the Reference Hypothesis score, these factors are combined as follows:

Hypothesis Score=(Effective Squares Score+Effective Amplitude Score+Effective Modulation Score)/3

Trace Based Metrics Application

The Trace Based Metrics are utilized as a module of the variant score differently for insertions, mismatches, and deletions.

1.) For mismatch variants, the KB hypothesis score and the reference hypothesis scores are the computed as previously described and carried forward into variant scoring.
2.) For insertion variants, the process follows from step 1 however the reference hypothesis score is always zero, as there is no reference module to consider.
3.) For deletion variants, the KB hypothesis score and the reference hypothesis score is computed as follows for the two points surrounding the location of the deletion and the average of these scores is passed forward. In the case of a missing base prior to or following the point of deletion, then the scores for the remaining base is carried forward. Deletions are further examined for missed bases. If a base has been missed, then the KB hypothesis score and the reference hypothesis score will be set to zero.

Missed bases are computed as follows:

1.) The query position sequence reflected in the Peak Record Database is examined to identify gaps in sequence. Should such a gap exist, then a missed base has occurred.
2.) If no such gap has occurred, the then between the peak before and after the considered peak, the trace distance is contemplated. If this distance exceeds a threshold, a missed base has occurred.

Combined Hypothesis Score

It is desirable to compute a single trace based hypothesis score to subsequently use in variant scoring. The combined hypothesis score is computed differently for mismatches, insertions, and deletions as follows:

1.) For mismatch variants, the combined hypothesis score is computed as follows:

Combined Hypothesis Score=min(max(KB Hypothesis Score−Reference Hypothesis Score,0),1)

2.) For insertion variants, the combined hypothesis score is computed as follows:

Combined Hypothesis Score=min(KB Hypothesis Score,1)

3.) For deletion variants, the combined hypothesis score is computed as follows:

If both the KB Hypothesis score and the Reference Hypothesis score are zero, then the combined hypothesis score is zero, otherwise compute:

Hypothesis Difference =
$$\min(\max(KB \text{ Hypothesis Score} - \text{Ref Hypothesis Score}, 0)1)$$

$$\text{Hypothesis Avg} = \frac{(KB \text{ Hypothesis Score} + \text{Ref Hypothesis Score})}{2}$$

Combined Hypothesis Score =
$$(1 - \text{Hypothesis Difference}) * \text{Hypothesis Average}$$

Other Trace Based Scores
Stutter Penalty

The stutter score is computed as described in the Trace Analysis section. The Stutter Penalty is computed as follows:

When stutter is associated in the trace, but not detected in the peak, the stutter penalty is computed as follows:

Stutter Penalty=(1.0−Stutter Score)*0.5

When stutter is detected in the scoring peak, the stutter score is computed as follows:

Stutter Penalty=1.0−Stutter Score

When no stutter is detected, the stutter penalty is set to 1.0.

End Score

Low quality base calls occur on the ends of virtually every Sanger read and must be removed by quality trimming to avoid incorrect variant calling. The quality trimming algorithm seeks a window (~20 bases) with a limited number of low quality bases (<4) within that window to define the clear range that should be algorithmically processed into variant calls. This quality trimming approach frequently incorporates a few low quality base calls in the clear range. This is undesirable when they cause false variant calls. Sometimes this approach includes just a few low quality base calls in the interior of the window, and this is desirable when it causes no harm and extends high-quality sequence before it. The algorithm's trace analysis is biased towards achieving concurrence with the KB called bases, and cannot be fully relied on to eliminate false positives that rise from included low-quality data on the ends. The following approach mitigates calling of false variants from low-quality base calls on the ends of reads.

Low-quality base calls may occur on the end of a read and which may give rise to false positive outcomes. Particularly as these portions of the reads tend to be unpaired, special processing is justified to avoid the false calls.

The End Score algorithm is implemented as follows:

Variants which occur within the region of the trace overlapping with the trimming window (typically 20 bases from the KB Call reference frame and extending into the clear range) are examined. The processing for mismatch and insertion variants is different than that for deletion variants.

For mismatch and insertion variants,
1.) The QV value produced by KB caller is examined for the peak of the called variant.
2.) If the QV value is below a certain threshold depending if the variant is pure-base or mixed-base, then a punishment is computed.
3.) The punishment is the ratio of the QV value and the threshold.
4.) The End Score is the greater of the maximum end-score penalty and the ratio.

For deletion variants,
1.) The QV value produced by KB caller is examined for the peak preceding and following the called variant.
2.) If the QV value is below a certain threshold depending if the variant is pure-base or mixed-base, then a punishment is computed.
3.) The punishment is the ratio of the QV value and the threshold.
4.) The End Score is the greater of the maximum end-score penalty and the ratio.

Low Modulation Score

The low modulation score is computed for each peak in the trace region as previously described in the Trace Analysis. The Low Modulation Score is computed differentially for mismatches and insertions and for deletion variants as follows:

1.) For mismatches and insertion variants, the low modulation score is the reported low modulation score.
2.) For deletion variants, the low modulation score is the average of the reported low modulation scores of the peak proceeding and the peak following the point of the deletion.

Combined Trace Score

It is desirable to produce a final combined trace score for input into variant scoring. The combined trace score is computed as follows:

Combined Trace Score=Combined Hypothesis Score*End Score*Stutter Penalty *Low Modulation Score Concordance Score The end user is able to aggregate samples into groups, which are experimental data produced from the same genomic material. These data could be provided by running forward and reverse assays for the same sample, or running multiple assays using different equipment or analysis settings. These samples provide a powerful mechanism that provides redundant observations to reinforce the trace analysis.

The concordance score is implemented as follows:
1.) For each variant observation, create a background population. That is a list of the imported reads which are in the same sample group, and whose clear range overlaps with the variant position.
2.) Screen the background to identify complementary reads. That is, if the variant is observed on a forward trace, only the reverse (complementary) traces can contribute to the concordance score. Likewise, if the variant is observed on a reverse trace, only the forward traces can contribute to the concordance score.
3.) For each relevant background read in an insertion and deletion variant:
   a. if the considered trace has no variant observation at the corresponding location, then increment the number of refuting observations,
   b. Otherwise if it has an identical observation increment the number of confirming observations.
   c. Compute the concordance score as:

$$\text{Concordance Score} = \frac{\text{number of confirmations}}{(\text{number of confirmations} + \text{number of refutes})}$$

4.) For each relevant background read in a mismatch variant:
   a. Attempt to reference the peak in the corresponding variant position from the background sequence.

b. If a corresponding peak cannot be retrieved, return a score of 0.5 (neutral.)
c. Confirm that the corresponding peak is compatible with the variant peak, that is for a pure base, it has the same peak detection and for a mixed-base it has the same two primary/secondary peak detections.
d. If the corresponding peak is not compatible with the variant peak, return 0.0 (strong refutation.)
e. Compute the concordance score as described below.

Compute Concordance Background Population

The background is created as follows:
1.) Consider all the reads which are in the same read group.
2.) Exclude the subject variant from the background population
3.) Ensure that the read is aligned with a passing quality
4.) Ensure that the read spans the region of the variant
5.) If the read includes an identical variant, add the variant to the background population.
6.) Otherwise, create a background variant, perform Trace Analysis on that variant, and add it to the background population.

Compute Mismatch Variant Concordance Score

The concordance score for mismatch variants is derived from trace analysis. The stringency applied for concordance is adjusted to be more speculative than the scoring tests applied previously.

The mismatch variant concordance score is computed as follows:
1.) Confirm that the corresponding peak is compatible with the variant peak; that is for a pure base, it has the same peak detection and for a mixed-base it has the same two primary/secondary peak detections.
2.) If the variant peak is pure:
  a. If the background peak's primary peak matches the variant peak, compute the concordance score from the squares score based on a linear mapping.
  b. Otherwise, if the background peak's secondary peak matches the variant peak then compute the concordance score from the secondary peak's squares score based on a linear mapping.
  c. Otherwise, compute the height and slope of the corresponding trace around the peak location. If the height of the peak's corresponding trace at the peak location is too low, return a concordance score of 0. If the slope is not strongly negative, then return a concordance score of 0. Otherwise, compute a concordance score based on the height of the peak using a linear mapping.
3.) If the variant peak is mixed:
  a. If the background peaks' primary and secondary bases match the variant peaks' primary and secondary bases, then compute the concordance score based on a linear mapping of the squares score for the background peak.
  b. If both peaks were found (but they were not primary and secondary) compute the concordance score based on the overlap of those peaks, using a linear mapping.
  c. If either peak, or both peaks were not found, compute the concordance scores as describe above in step 2c.

Compute Variant Score

For each variant, the variant score is computed from the trace score and the concordance score as follows. Note that the concordance score can either strengthen or weaken the results of the trace score to a degree proportional to the trace score and adjusted by a gain.

Effective Trace Score=Trace Score*Trace Score Gain

Effective Concordance Score=(Concordance Score−Concordance Score Bias)*(Effective Trace Score*Concordance Score Gain)

Variant Score=min(max(Trace Score+Concordance Score,0.0)1.0)

Error! Reference source not found. 37 shows the performance of the variant scoring to discriminate true positive and false positive outcomes. The performance provides a range of adjustments to the user to enhance detection and to enhance rejection.

Computer-Implemented System

Those skilled in the art will recognize that the operations of the various embodiments may be implemented using hardware, software, firmware, or combinations thereof, as appropriate. For example, some processes can be carried out using processors or other digital circuitry under the control of software, firmware, or hard-wired logic. (The term "logic" herein refers to fixed hardware, programmable logic and/or an appropriate combination thereof, as would be recognized by one skilled in the art to carry out the recited functions.) Software and firmware can be stored on non-transitory computer-readable media. Some other processes can be implemented using analog circuitry, as is well known to one of ordinary skill in the art. Additionally, memory or other storage, as well as communication modules, may be employed in embodiments of the invention.

Figure 38:
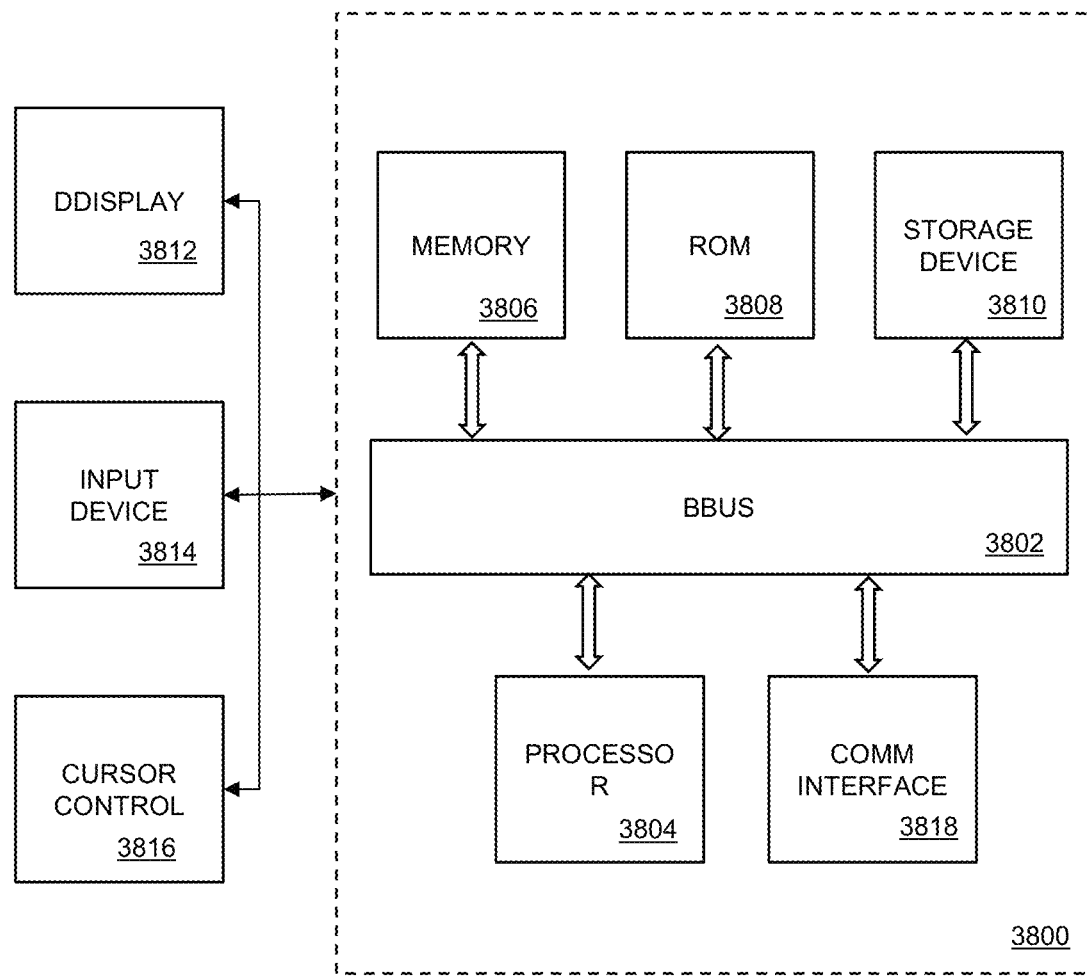
FIG. 38 illustrates an exemplary computing system for implementing various embodiments described herein.

FIG. 38 is a block diagram that illustrates a computer system 3800 that may be employed to carry out processing functionality, according to various embodiments. Instruments to perform experiments may be connected to the exemplary computing system 3800. Computing system 3800 can include one or more processors, such as a processor 3804. Processor 3804 can be implemented using a general or special purpose processing engine such as, for example, a microprocessor, controller or other control logic. In this example, processor 3804 is connected to a bus 3802 or other communication medium.

Further, it should be appreciated that a computing system 3800 of FIG. 38 may be embodied in any of a number of forms, such as a rack-mounted computer, mainframe, supercomputer, server, client, a desktop computer, a laptop computer, a tablet computer, hand-held computing device (e.g., PDA, cell phone, smart phone, palmtop, etc.), cluster grid, netbook, embedded systems, or any other type of special or general purpose computing device as may be desirable or appropriate for a given application or environment. Additionally, a computing system 3800 can include a conventional network system including a client/server environment and one or more database servers, or integration with LIS/LIMS infrastructure. A number of conventional network systems, including a local area network (LAN) or a wide area network (WAN), and including wireless and/or wired modules, are known in the art. Additionally, client/server environments, database servers, and networks are well documented in the art. According to various embodiments described herein, computing system 3800 may be configured to connect to one or more servers in a distributed network. Computing system 3800 may receive information or updates from the distributed network. Computing system 3800 may also transmit information to be stored within the distributed network that may be accessed by other clients connected to the distributed network.

Computing system 3800 may include bus 3802 or other communication mechanism for communicating information, and processor 3804 coupled with bus 3802 for processing information.

Computing system 3800 also includes a memory 3806, which can be a random access memory (RAM) or other dynamic memory, coupled to bus 3802 for storing instructions to be executed by processor 3804. Memory 3806 also may be used for storing temporary variables or other intermediate information during execution of instructions to be executed by processor 3804. Computing system 3800 further includes a read only memory (ROM) 3808 or other static storage device coupled to bus 3802 for storing static information and instructions for processor 3804.

Computing system 3800 may also include a storage device 3810, such as a magnetic disk, optical disk, or solid state drive (SSD) is provided and coupled to bus 3802 for storing information and instructions. Storage device 3810 may include a media drive and a removable storage interface. A media drive may include a drive or other mechanism to support fixed or removable storage media, such as a hard disk drive, a floppy disk drive, a magnetic tape drive, an optical disk drive, a CD or DVD drive (R or RW), flash drive, or other removable or fixed media drive. As these examples illustrate, the storage media may include a computer-readable storage medium having stored therein particular computer software, instructions, or data.

In alternative embodiments, storage device 3810 may include other similar instrumentalities for allowing computer programs or other instructions or data to be loaded into computing system 3800. Such instrumentalities may include, for example, a removable storage unit and an interface, such as a program cartridge and cartridge interface, a removable memory (for example, a flash memory or other removable memory module) and memory slot, and other removable storage units and interfaces that allow software and data to be transferred from the storage device 3810 to computing system 3800.

Computing system 3800 can also include a communications interface 3818. Communications interface 3818 can be used to allow software and data to be transferred between computing system 3800 and external devices. Examples of communications interface 3818 can include a modem, a network interface (such as an Ethernet or other NIC card), a communications port (such as for example, a USB port, a RS-232C serial port), a PCMCIA slot and card, Bluetooth, etc. Software and data transferred via communications interface 3818 are in the form of signals which can be electronic, electromagnetic, optical or other signals capable of being received by communications interface 3818. These signals may be transmitted and received by communications interface 3818 via a channel such as a wireless medium, wire or cable, fiber optics, or other communications medium. Some examples of a channel include a phone line, a cellular phone link, an RF link, a network interface, a local or wide area network, and other communications channels.

Computing system 3800 may be coupled via bus 3802 to a display 3812, such as a cathode ray tube (CRT) or liquid crystal display (LCD), for displaying information to a computer user. An input device 3814, including alphanumeric and other keys, is coupled to bus 3802 for communicating information and command selections to processor 3804, for example. An input device may also be a display, such as an LCD display, configured with touchscreen input capabilities. Another type of user input device is cursor control 3816, such as a mouse, a trackball or cursor direction keys for communicating direction information and command selections to processor 3804 and for controlling cursor movement on display 3812. This input device typically has two degrees of freedom in two axes, a first axis (e.g., x) and a second axis (e.g., y), that allows the device to specify positions in a plane. A computing system 3800 provides data processing and provides a level of confidence for such data. Consistent with certain implementations of embodiments of the present teachings, data processing and confidence values are provided by computing system 3800 in response to processor 3804 executing one or more sequences of one or more instructions contained in memory 3806. Such instructions may be read into memory 3806 from another computer-readable medium, such as storage device 3810. Execution of the sequences of instructions contained in memory 3806 causes processor 3804 to perform the process states described herein. Alternatively hard-wired circuitry may be used in place of or in combination with software instructions to implement embodiments of the present teachings. Thus implementations of embodiments of the present teachings are not limited to any specific combination of hardware circuitry and software.

The term "computer-readable medium" and "computer program product" as used herein generally refers to any media that is involved in providing one or more sequences or one or more instructions to processor 3804 for execution. Such instructions, generally referred to as "computer program code" (which may be grouped in the form of computer programs or other groupings), when executed, enable the computing system 3800 to perform features or functions of embodiments of the present invention. These and other forms of non-transitory computer-readable media may take many forms, including but not limited to, non-volatile media, volatile media, and transmission media. Non-volatile media includes, for example, solid state, optical or magnetic disks, such as storage device 3810. Volatile media includes dynamic memory, such as memory 3806. Transmission media includes coaxial cables, copper wire, and fiber optics, including the wires that comprise bus 3802.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 3804 for execution. For example, the instructions may initially be carried on magnetic disk of a remote computer. The remote computer can load the instructions into its dynamic memory and send the instructions over a telephone line using a modem. A modem local to computing system 3800 can receive the data on the telephone line and use an infra-red transmitter to convert the data to an infra-red signal. An infra-red detector coupled to bus 3802 can receive the data carried in the infra-red signal and place the data on bus 3802. Bus 3802 carries the data to memory 3806, from which processor 3804 retrieves and executes the instructions. The instructions received by memory 3806 may optionally be stored on storage device 3810 either before or after execution by processor 3804.

It will be appreciated that, for clarity purposes, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

Distributed System

Figure 39:
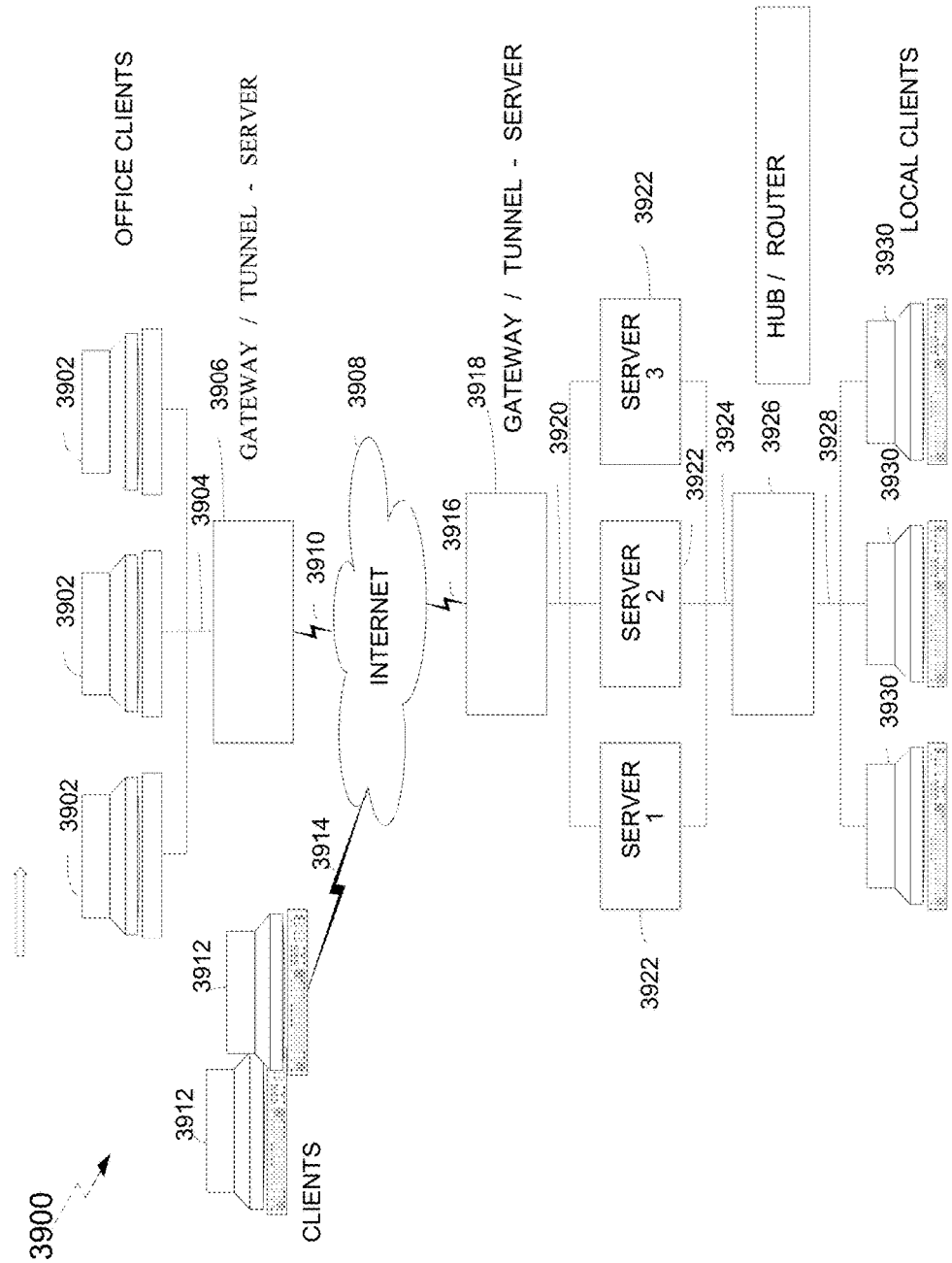
FIG. 39 illustrates an exemplary distributed network system according to various embodiments described herein.

Some of the elements of a typical Internet network configuration 600 are shown in FIG. 39, wherein a number of client machines 3902 possibly in a remote local office, are shown connected to a gateway/hub/tunnel-server/etc 3910 which is itself connected to the internet 3908 via some internet service provider (ISP) connection 3910. Also shown are other possible clients 3912 similarly connected to the internet 3908 via an ISP connection 3914, with these units communicating to possibly a central lab or office, for example, via an ISP connection 3916 to a gateway/tunnel-server 3918 which is connected 3920 to various enterprise application servers 3922 which could be connected through another hub/router 3926 to various local clients 3930. Any of these servers 3922 could function as a development server for the analysis of potential content management and delivery design solutions as described in the present invention, as more fully described below.

Although various embodiments have been described with respect to certain exemplary embodiments, examples, and applications, it will be apparent to those skilled in the art that various modifications and changes may be made without departing from the present teachings.

What is claimed is:

1. A method for detecting nucleic acid sequence variants in electropherogram data produced by nucleic acid sequencing, the method comprising:
   receiving electropherogram data comprising one or more nucleic acid sequences from an instrument wherein the nucleic acid sequences are imported into one or more query sequence records and are validated using a translation table as indicating one or more valid pure bases or one or more valid mixed bases;
   analyzing the electropherogram data to identify mixed bases in the electropherogram data including detecting an orientation of each of the one or more nucleic acid sequences and identifying a best it mixed-base alignment between the query sequence record and a reference sequence record;
   identifying features within the electropherogram data indicative of errors wherein an error is indicated where one or more sequence features do not fall within an acceptable range or where an alignment level between the query sequence record and the reference sequence record does not fall within an acceptable range;
   validating the identified mixed base by importing analyzed trace data and extracting peak location data for each of four electropherogram channels; and
   determining variants in the electropherogram data based on detecting one or more peaks in the electropherogram data for the validated mixed bases.

2. The method of claim 1, wherein analyzing the electropherograni data to identify mixed bases includes determining a mixed-base alignment.

3. The method of claim 1, wherein validating the identified mixed bases comprises:
   detecting peaks in the electropherogram data;
   detecting intersections in the electropherogram data; and
   detecting stutter peaks in the electropherogram data.

4. The method of claim 3, wherein validating the identified mixed bases further comprises:
   mapping the detected peaks.

5. The method of claim 3, wherein validating the identified mixed bases further comprises:
   merging the peaks based on the detected peaks; the detected intersections, and the detected stutter peaks.

6. The method of claim 1, further comprising:
   validating the determined variants based on generating a score based on the identified features.

7. A system for detecting variants in electropherogram data produced by nucleic acid sequencing, the system comprising:
   an input module configured to receive electropherogram data comprising one or more nucleic acid sequences from an instrument wherein the nucleic acid sequences are imported into one or more query sequence records and are validated using a base translation table as indicating one or more valid pure bases or one or more valid mixed bases;
   a mixed base variant validator module to identify mixed bases in the electropherogram data including detecting an orientation of each of the one or more nucleic acid sequences and identifying a best fit mixed-base alignment between the query sequence record and a reference sequence record, identify features within the electropherogram data indicative of errors wherein an error is indicated where one or more sequence features do not fall within an acceptable range or where an alignment level between the query sequence record and the reference sequence record does not fall within an acceptable range, and validate the identified mixed bases by importing analyzed trace data and extracting peak location data for each of four electropherogram channels; and
   a variant caller configured to determine variants in the electropherogram data based on detecting one or more peaks in the electropherogram data for the validated mixed bases.

8. The system of claim 7, further comprising:
   an alignment module configured to analyze the electropherogram data to determine a mixed-base alignment.

9. The system of claim 7, further comprising:
   a stutter and peak detector configured to identify features within the electropherogram data indicative of errors.

10. The system of claim 7, further comprising:
    a variant score generator configured to validate variants in the electropherogram data.

11. A computer-readable storage medium encoded with processor executable instructions for detecting nucleic acid sequence variants in electropherogram data produced by nucleic acid sequencing, the instructions comprising instructions for:
   receiving electropherogram data comprising one or more nucleic acid sequences from an instrument wherein the nucleic acid sequences are imported into one or more query sequence records and are validated using a base translation table as indicatingnne or more valid pure bases or one or more valid mixed bases:
   analyzing the electropherogram data to identify mixed bases in the electropherogram data including detecting an orientation of each of the one or more nucleic acid sequences and identifying a best fit mixed-base alignment between the query sequence record and a reference sequence record;
   identifying features within the electropherogram data indicative of errors, wherein an error is indicated where one or more sequence features do not fall within an acceptable range or where an alignment level between the query sequence record and the reference sequence record does not fall within an acceptable range;
   validating the identified mixed bases by importing analyzed trace data and extracting peak location data for each of four electropherogram channels; and determining variants in the electropherogram data based on detective one or more peaks in the electropherogram data for the validated mixed bases.

12. The method of claim 11, wherein analyzing the electropherogram data to identify mixed bases includes determining a mixed-base alignment.

13. The method of claim 11, wherein validating the identified mixed bases comprises:
  detecting peaks in the electropherogram data;
  detecting intersections in the electropherogram data; and
  detecting stutter peaks in the electropherogram data.

14. The computer-readable storage medium of claim 13, wherein the instructions for validating the identified mixed bases further comprises instructions for:
  mapping the detected peaks.

15. The computer-readable storage medium of claim 13, wherein the instructions for validating the identified mixed bases further comprises instructions for:
  merging the peaks based on the detected peaks, the detected intersections, and the detected stutter peaks.

16. The computer-readable storage medium of claim 11, further comprising instructions for:
  validating the determined variants based on generating a score based on the identified features.

\* \* \* \* \*